United States Patent [19]
Goldberg et al.

[11] Patent Number: 5,108,776
[45] Date of Patent: * Apr. 28, 1992

[54] OCULAR IMPLANTS AND METHODS FOR THEIR MANUFACTURE

[75] Inventors: Eugene P. Goldberg; Ali Yahiaoui, both of Gainesville, Fla.

[73] Assignee: University of Florida, Gainesville, Fla.

[ * ] Notice: The portion of the term of this patent subsequent to Feb. 21, 2006 has been disclaimed.

[21] Appl. No.: 592,478

[22] Filed: Oct. 5, 1990

Related U.S. Application Data

[63] Continuation-in-part of Ser. No. 304,479, Feb. 1, 1989, Pat. No. 4,961,954, which is a continuation-in-part of Ser. No. 37,153, Apr. 10, 1987, Pat. No. 4,806,382.

[51] Int. Cl.$^5$ ............ A01N 1/02; B05D 3/06
[52] U.S. Cl. ............................ 427/2; 427/36; 522/84; 522/85; 522/167; 623/4; 623/5; 623/6; 623/901
[58] Field of Search .......... 427/2, 36; 522/84, 85, 522/167; 623/6, 901, 4, 5

[56] References Cited

U.S. PATENT DOCUMENTS

| 4,806,382 | 2/1989 | Goldberg et al. | 427/2 |
| 4,897,433 | 1/1990 | Sugo et al. | 427/2 X |
| 4,955,901 | 9/1990 | Nishiguchi et al. | 427/40 X |
| 5,007,928 | 4/1991 | Okamura et al. | 427/2 X |

*Primary Examiner*—Michael Lusignan
*Attorney, Agent, or Firm*—Kerkam, Stowell, Kondracki & Clarke

[57] ABSTRACT

An improved method for modifying the surface of an ocular implant material by the gamma or electron beam irradiation induced chemical graft coating thereon of a monomer comprising N-vinly-pyrrolidone, 2-hydroxyethylmethacrylate or a mixture of the two to form a hydrophilic graft polymer coating, the improvement comprising pre-soaking the ocular implant material in a monomer or a solution comprising a monomer prior to conducting the gamma- or electron beam-irradiation induced graft polymerization in a second solution of a monomer.

17 Claims, 7 Drawing Sheets

OCULAR IMPLANTS AND METHODS FOR THEIR MANUFACTURE

BACKGROUND OF THE INVENTION

Related Applications

This application is a continuation-in-part of application Ser. No. 304,479, filed Feb. 1, 1989, now U.S. Pat. No. 4,961,954, issued Oct. 9, 1990, which is a continuation-in-part of application Ser. No. 037,153, filed Apr. 10, 1987, now U.S. Pat. No. 4,806,382, issued Feb. 21, 1989.

FIELD OF THE INVENTION

The present invention relates to ocular implants and methods for improving surfaces thereof.

PRIOR ART

Studies have shown that the surgical implantation of ocular implants such as intraocular lenses (IOL), etc., can result in the loss of significant corneal endothelial tissue unless great care is taken to ensure a lack of contact between the device and the endothelium. Most ocular implants are constructed of hydrophobic polymethylmethacrylate (PMMA) polymers because of their superior optical qualities, resistance to biodegradation, etc. It has been found, however, that PMMA surfaces adhere to endothelial cells upon even casual contact and that separation of the surface therefrom results in a tearing away of the endothelial tissue adhered to the polymer surface. Similar adhesive interactions with other ocular tissues, i.e., the iris, can also cause adverse tissue damage. Other hydrophobic polymers which are used or have been proposed for use in ocular implants (i.e., polypropylene, polyvinylidene fluoride, polycarbonate, polysiloxane) also can adhere to ocular tissue and thereby promote tissue damage.

It is well documented in the prior art that a significant disadvantage inherent in PMMA IOLs resides in the fact that any brief, non-traumatic contact between corneal endothelium and PMMA surfaces results in extensive damage to the endothelium. See Bourne et al, Am. J. Ophthalmol., Vol. 81, pp. 482–485 (1976); Forster et al, Trans. Am. Acad. Ophthalmol. Otolaryngol., Vol. 83, OP-195-OP-203 (1977); Katz et al, Trans Am. Acad. Ophthalmol. Otolaryngol., Vol. 83, OP-204-OP-212 (1977); Kaufman et al, Science, Vol. 198, pp. 525–527 (1977) and Sugar et al, Arch. Ophthalmol., Vol. 96, pp. 449–450 (1978) for a discussion of the problem associated with implant surface/endothelium contact.

Since it is extremely difficult to avoid any contact between implant surfaces and endothelium during surgical procedures and especially to other sensitive ocular tissues during implant life, i.e., the iris, ciliary sulcus, etc., efforts have been undertaken to modify the PMMA ocular implant surfaces to reduce the tendency thereof to adhere to and damage corneal endothelium.

Ocular implant surfaces have been coated with various hydrophilic polymer solutions or temporary soluble coatings such as methylcellulose, polyvinylpyrrolidone (Katz et al and Knight et al, supra), etc., to reduce the degree of adhesion between the implant surfaces and tissue cells. While offering some temporary protection, these methods have not proven entirely satisfactory since such coatings complicate surgery, do not adhere adequately to the implant surfaces, become dislodged or deteriorate after implantation, dissolve away rapidly during or soon after surgery or may produce adverse post-operative complications. Moreover, it is difficult to control the thicknesses and uniformity of such coatings.

Yalon et al [Acta: XXIV, International Congress of Ophthalmology, ed. Paul Henkind (1983)] and Knight et al [Chem. Abs., Vol. 92:203547f (1980)] have reported attempts to produce protective coatings on PMMA implant surfaces by gamma-radiation induced polymerization of vinylpyrrolidone thereon. Their efforts were not altogether successful, however, since their methods also presented problems in controlling the optical and tissue protective qualities of the coatings. Process conditions and parameters (i.e., monomer concentration solvent, dose and dose rate) were not specified. The resulting coatings were of poor quality and non-uniform mechanical stability.

In U.S. Pat. No. 4,806,382, issued Feb. 21, 1989, there are described improved methods for producing hydrophilic, gamma irradiation induced polymerized and chemically grafted coatings on ocular implants constructed of a variety of polymeric materials, which methods overcome the above-noted difficulties and disadvantages.

The invention described in that patent is predicated on the discovery of certain process conditions and parameters that produce thin hydrophilic gamma irradiation induced polymerized and chemically grafted coatings of N-vinyl-pyrrolidone (NVP) [PVP], copolymerized NVP and 2-hydroxyethylmethacrylate (HEMA) [P(NVP-HEMA)], or HEMA [PHEMA] and their copolymers, particularly with ionic comonomers on the surfaces of ocular implants constructed of materials including polymethylmethacrylate (PMMA) and of other process conditions and parameters which produce thin gamma irradiation induced graft PVP, P(NVP-HEMA), PHEMA, or copolymer coatings on the surfaces of ocular implant articles constructed of materials including polypropylene (PP), polyvinylidene fluoride (PVDF), polycarbonate (PC) and polysiloxane or silicone (PDMSO). The coatings increase the hydrophilicity of the implant surface and minimize adhesion between the surface and sensitive ocular tissues such as corneal endothelium or iris thereby minimizing tissue damage and post-operative complications occasioned by contact between the implant surface and ocular tissue. The coatings produced by the improved method of the invention described in U.S. Pat. No. 4,806,382 are thin and uniform. Moreover, they are chemically bound to the surface of the ocular implant and, therefore, far more durable and less subject to removal, degradation or deterioration during or following surgery than the coatings produced by prior art methods.

The improved gamma-irradiation induced graft polymerization of NVP, HEMA or mixtures of NVP and HEMA on ocular implant surfaces comprising PMMA to form optimum PVP, P(NVP-HEMA) or PHEMA graft polymer surface modifications thereon described in U.S. Pat. No. 4,806,382 comprises carrying out the graft polymerization in an aqueous solution under specific combinations of the following conditions:

a) monomer concentration in the range of from about 0.5 to about 50%, by weight;

b) total gamma dose in the range of from about 0.01 to about 0.50 Mrad;

c) gamma dose rate in the range of from about 10 to about 2500 rads/minute; and d) maintaining the molecular weight of the polymer in solution in the range of from about 250,000 to about 5,000,000.

The maintenance of the molecular weight of the polymer in solution at certain values, identified in U.S. Pat. No. 4,806,382, as a critical condition of the method is not actually a "condition" of the method, but rather, as stated in the specification, a result which is dependent on the reaction conditions employed in carrying out the graft polymerization process. It is, therefore, not appropriate to specify the molecular weight of the polymer in solution as a process "condition" since it is rather an outcome of the reaction conditions used in this invention and may be widely varied depending on specific gamma graft monomer-substrate-process conditions. If a certain set of fixed conditions are employed, namely: monomer, monomer concentration, total gamma dose, gamma dose rate and radical polymerization inhibitors, the molecular weight of the polymer formed in solution will be an output of the process which is dependent upon the values of the above-noted monomer, monomer concentration, total gamma dose, gamma dose rate and radical polymerization inhibitor conditions. For example, in the presence of certain ionic monomers, solvents, or radical inhibitors, solution polymerization may be inhibited significantly without sacrificing efficient surface graft polymerization and the resulting solution polymer molecular weight may thereby be relatively low (i.e., as low as 5,000-10,000).

Since the application which matured into U.S. Pat. No. 4,806,382 was filed, the inventors of the subject matter defined therein conducted additional research and unexpectedly found that although relatively low doses of 0.01 to 0.20 Mrad are generally preferred for the compositions of this invention, the process could be conducted at a total gamma dose as low as 0.001 Mrad.

The state of the art prior to the application which matured into U.S. Pat. No. 4,806,382 taught the use of relatively high gamma doses, generally greater than 0.5 Mrad, for gamma polymerization grafting, and it was therefore surprising to find that surface grafting could be achieved at doses as low as 0.01 Mrad. The achievement of effective grafting at doses as low as 0.001 Mrad is consequently an even more unexpected result of the process of this invention. Furthermore, although grafting with monomer concentrations as low as 0.5 wt % was indicated in prior U.S. Pat. No. 4,806,382, further research has revealed that monomer concentrations as low as 0.1 wt % may be utilized in some embodiments of the graft process of this invention.

Optimally, the method may also be carried out under one or more of the following conditions:

e) substantially excluding free oxygen from the aqueous graft polymerization solution;

f) maintaining the thickness of the PVP or P(NVP-HEMA) surface graft in the range of from about 100 Å to about 150 microns;

g) including a free radical scavenger in the aqueous graft polymerization solution; and h) including in the aqueous graft polymerization solution a swelling solvent for PMMA or other polymer substrate surface.

The improved gamma-irradiation induced graft polymerization of NVP, mixtures of NVP and HEMA, HEMA, other hydrophilic monomers or their copolymers on ocular implant surfaces comprising PP, PVDF, PC or PDMSO to form optimum PVP or P(NVP-HEMA) surface grafts thereon may also be carried out under specific combinations of the process parameters as indicated above for PMMA but also under conditions which involve excluding free oxygen from the polymerization solution for preferred surface modification of these ocular implant polymer substrates.

It is an object of the present invention to provide a still further improved method for producing hydrophilic polymer graft surface modifications on ocular implant materials.

SUMMARY OF THE INVENTION

The present invention is predicated on the discovery that the methods described in U.S. Pat. No. 4,806,382, issued Feb. 21, 1989, are significantly simplified and improved by first pre-soaking the ocular implant surface to be surface modified in an aqueous solution of the monomer or the monomer itself in certain cases prior to graft polymerizing the monomer onto the surface from an aqueous monomer solution.

The invention also includes ocular implant materials and ocular implant devices produced according to the above-described procedures.

BRIEF DESCRIPTION OF THE DRAWINGS

FIG. 1 depicts a top view of a one-piece intraocular lens,

FIG. 2 depicts a top view of an intraocular lens with fiber haptics which may be made of a different substrate polymer than the optic, and FIG. 3 depicts a top view of a keratoprosthesis.

DETAILED DESCRIPTION OF THE INVENTION

Figure 1:
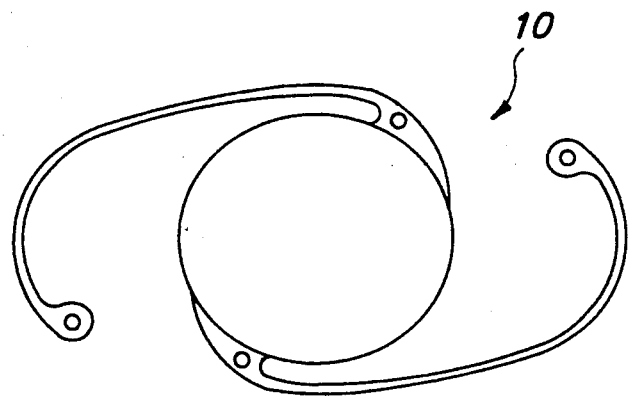
FIGS. 1–3 depict examples of ocular implants according to the present invention.
Figure 2:
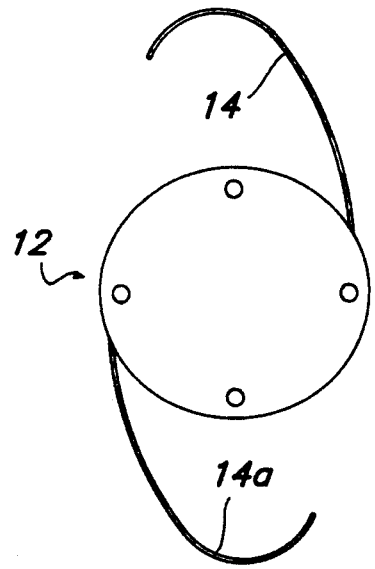
Figure 3:
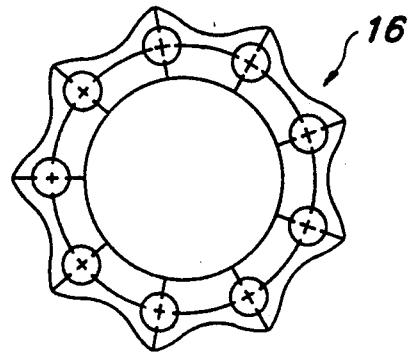

The entire disclosure of U.S. Pat. No. 4,806,382 is incorporated herein by reference. Yalon et al (supra) and Knight et al (supra) disclose gamma-irradiation coatings on PMMA using N-vinylpyrrolidone (NVP) and 2-hydroxyethylmethacrylate (HEMA) and indicate poor dynamic (abrasive) protection of endothelium for these coatings. Dissolvable coatings of polyvinylalcohol (PVA) were regarded as optimal for (IOLs) by Knight et al, supra, and commerical development of a PVA-coated IOL was attempted with unsatisfactory clinical results. The gamma polymerization surface modifications reported were carried out under process conditions of monomer concentration, solvent, dose and dose rate which were not specified and which apparently yielded poor quality, readily abraded coatings. Conditions for producing useful permanent PVP or PHEMA coatings on PMMA IOLs are not taught in the prior art. Neither Knight et al, Yalon et al or the literature on gamma-graft polymerization of the past 30 years suggest the process conditions required to achieve the complicated requirements for useful ocular implant coatings. These requirements include:

a) Thin, permanent, optically clear and uniform graft coatings for the optic. The literature generally discloses conditions which produce distortion and degradation of the substrate due to the use of high gamma-radiation doses (>1 Mrad) and non-aqueous solvent media, and yield thick, cloudy, non-uniform coatings as well as highly viscous gel-like solutions of the grafting polymer which makes grafted substrate removal and washing very difficult (e.g., Chapiro, *Radiation Chemistry of*

Polymeric Systems, John Wiley and Sons, Inc., New York, 1962; Henglein et al, Angew. Chem., Vol. 15, p. 461 (1958).

b) Long-term biocompatibility in the eye (e.g., at least one year satisfactory behavior in rabbit eye implants).

c) Low contact angle (high wettability) for water or underwater air bubble (less than about 30°).

d) Less adherent to tissue and to lens epithelial cells from culture (adhesive force to endothelium and number of cells per unit area less than about 50% of that observed for PMMA).

e) Non-damaging to endothelium (less than ca. 20% damage for in vitro contact tests).

f) Measurable graft coating by ESCA or FTIR spectroscopy or by optical or electron microscopy.

g) Abrasion resistance by sliding (dynamic) friction testing showing no change in wetting (contact angle) and confirming before and after presence of graft coating.

h) Rapid hydration—change from dry state to wetted lubricous state on immersion in water (within five minutes).

Yalon et al (supra) disclose an in vitro technique for measuring endothelium damage. Results for PMMA were used to illustrate the method. Although it was noted that PVP coatings reduced cell damage with less damage at higher monomer concentrations, the conditions for the experiment (i.e., irradiation dose, dose rate, etc.) were not disclosed nor were any of the critical process-product relationships indicated.

The improved process conditions and parameters of the invention described in U.S. Pat. No. 4,806,382, which are necessary to produce useful ocular implant polymers having a surface modified by gamma-irradiation induced graft polymerization therein of PVP, P(NVP-HEMA)- or PHEMA include: % monomer, gamma dose, dose rate and oxygen (air) degassing. Other optimal process conditions include catalysts, free radical scavengers, PMMA swelling solvents, and temperature. The solution polymer molecular weight and M.W. distribution, the % conversion and residual monomer, the graft polymer thickness and surface properties, etc., are process results which can change markedly as the process variables change. For example, the surface modification achieved for PVP on PMMA will be different when using 10% monomer and 0.1 Mrad if prepared at low dose rates since low dose rates (slower polymerization) favor higher molecular weights. Similarly, degassed oxygen-free reactions result in improved grafts at much lower doses. The presence of free radical scavengers such as copper or iron salts or organic reducing agents (i.e., ascorbic acid) also greatly influences other process parameters, generally reducing solution polymer molecular weight and preventing solution gelation at high monomer concentrations.

Each of the above-described process conditions and parameters may be varied within the ranges discussed below to produce certain specific combinations which are particularly advantageous for the surface modified ocular article polymers.

(a) Monomer concentration: Increasing monomer concentration increases polymer mol. wt. in the graft solution and reduces contact angle (C.A.), i.e., renders the surface more hydrophilic. For example, in the case of forming PVP coatings on PMMA, in the range of from about 3-15% NVP the PVP viscosity mol. wt. ($M_v$) increases from 560,000 to 2,700,000 and the PMMA graft C.A. decreases from 29° to 21° at 0.1 Mrad and 309 rads/min. However, this effect is sensitive to dose rate and total dose. For example, at 1-10% NVP, but at a lower dose rate of 64 rads/min., the mol. wt. increases from 400,000 to 4,590,000 and the C.A. decreases from 49° to 18°.

In general, monomer concentrations in the range of 0.1-50% are preferred depending on other parameters. Concentrations as low as 0.1 to 0.5% at low dose rates can yield hydrophilic surface grafts with C.A. below 30°-40° under conditions of this invention. At monomer concentrations greater than 20-30%, effective grafting without solution polymer gelation requires low doses and use of free radical scavengers. Monomer concentrations greater than 50% are feasible but not preferred since high concentrations of radical scavengers must be used and polymer mol. wts. and monomer conversion are lowered significantly by their use. For producing PHEMA coatings, HEMA concentrations of between 0.5% and 10%, by weight, are sufficient.

(b) Dose: In general, increasing total gamma dose increases mol. wt. of the polymer and reduces C.A. However, an important practical limit exists in that at higher doses, lower dose rates, and higher monomer concentrations, reaction media becomes extremely viscous or form gels which are very difficult to wash and to remove (e.g., about 0.25 Mrad and 10% NVP at 309 rads/min).

It will be understood by those skilled in the art that electron beam radiation will also induce graft polymerization. Therefore, electron beam radiation of energies equivalent to that described herein for gamma radiation may be substituted for gamma radiation in the practice of the method of the invention. Electron beam voltages in the range of from about 50 KeV to about 10 MeV may be employed at currents of from about 5 mA to about 100 mA. For electron beam initiated polymerization grafting, conditions which produce dose rates substantially higher than for gamma graft polymerization, i.e., in the range of from about 10 to about $10^8$ rads/min or more may be employed.

(c) Dose rate: Decreasing gamma radiation dose rate generally increases solution PVP M.W., e.g., from 1,150,000 to 5,090,000 at 10% NVP and 0.1 Mrad as dose rate decreases from 1235 to 49 rads/min. The C.A. also goes down at lower dose rates, i.e., from 31° to 15°. As noted above, dose rates of up to $10^8$ rads/min or more are practical when employing electron beam irradiation.

(d) Solution Polymer Mol. Wt.: The mol. wt. may vary widely depending upon process conditions, monomers and radical inhibitors used. Effective grafting with low C.A. may therefore be achieved with even low mol. wt. solution polymer ($M_v$ as low as 5000-10,000). However, solution polymer $M_v$ greater than 5,000,000 or gels which form during grafting are generally impractical because of washing problems.

(e) Degassing: Removal of oxygen from the graft solutions by vacuum and/or inert gas (e.g., argon purging) has an important effect: lower total doses are required (practical grafting at less than 0.1 Mrad). Oxygen degassing also has a large effect on PVP $M_w$ and % conversion of monomer. For example, with degassing, good grafting of PVP on polypropylene (PP) is achieved at 0.05 Mrad and 10% NVP (C.A. 15°). Without degassing, little grafting occurs under these conditions. Oxygen degassing is critical to hydrophilic surface modification grafting where the substrate polymer is PP, PVDF or PDMSO. It has been found that graft polymerization is inefficient when using these materials as substrates in the presence of oxygen. Oxygen degassing is also beneficial for PMMA and PC substrates in that much lower radiation doses (0.01–0.15 Mrad) become effective compared with grafting these polymers in the presence of oxygen.

f) Graft thickness: Surface grafts less than 100–200 Å, although non-adhesive and hydrophilic, are useful but may exhibit somewhat less mechanical "softness" or compliant gel-like surfaces than thicker coatings for reduced tissue-contact trauma. Graft coatings greater than ca. 300–500 Å (or 0.03–0.05 microns) up to 50 microns or more are probably more desirable for many applications as long as they are smooth, uniform, optically clear for optic surfaces, and quickly hydrated.

Using no swelling solvents and no prolonged monomer contact with substrates prior to irradiation, surface grafts which exhibit desired implant properties under preferred process conditions have thicknesses of about 0.1 to 5 microns. However, using swelling solvents such as ethyl acetate, polymer grafts on PMMA of 100 microns or more can be prepared. For certain applications it may be preferred to have thicker "spongy" coatings of 20–100 microns.

g) Free-Radical Scavengers: Free radical traps, usually reducing agents such as $Cu^+$, $Fe^{+2}$ ascorbic acid, etc., are known to inhibit radical polymerization in solution and thus be effective (especially at high gamma doses, high dose rates, and high monomer concentrations) in slowing the onset of solution gelation during grafting. However, under practical grafting conditions, this may result in lower mol. wts., high concentrations of unreacted monomer and broad mol. wt. distributions. Use of metal salts may also be objectionable where maximum biocompatibility is critical.

Although most preferred graft conditions avoid the use of radical scavengers, useful conditions for graft coatings of PVP, P(NVP-HEMA) or PHEMA have also been defined using ascorbic acid to limit high viscosity and gelation of the graft polymer solution. These conditions use high monomer concentrations (up to 50%) and thicker grafts are obtained using ethyl acetate as a swelling solvent (0.5–5%).

(h) Swelling solvents: The use of substrate polymer solvents in the aqueous monomer grafting solution facilitates swelling and monomer diffusion into the polymer before and during gamma polymerization. Penetration of monomers into the substrate increases graft coating thickness and enhances bonding to the surface. Solvents such as ethyl acetate have been shown to greatly facilitate this process with some substrates such as PMMA.

Although the above-described method represents a significant improvement over prior art methods, optimum results in each case depend upon the selection of a combination of numerous process parameters and conditions.

The foregoing method is greatly simplified and the surface grafts are significantly enhanced by the method of the present invention according to which the substrate to be surface-modified is pre-soaked in the grafting monomer (or mixture of monomers) or in a first aqueous solution having a concentration of from about 5% to about 95%, by weight, of the grafting monomer (or mixture of monomers) for a period of time and at a temperature sufficient to facilitate diffusion of the monomers(s) into the substrate surface. This pre-soaking step avoids the necessity for utilizing organic swelling solvents. These swelling solvents unduly complicate the final coating procedure since they must be completely washed away and may promote crazing or cracking of the substrate polymers.

The monomer pre-soaking method of the present invention results in a controlled diffusion of monomer into the substrate and may often produce what may be regarded as an interpenetrating subsurface polymer structure for the ultimately formed hydrophilic polymer graft surface modification. The latter is rendered more durable by the thus formed anchoring substructure. This monomer pre-soak improvement is also beneficially conducted with mixed monomers wherein one hydrophilic monomer is used as the pre-soak monomer and a second hydrophilic monomer is used for the subsequent gamma polymerization grafting step. This is particularly advantageous, for example, with polysiloxane surface modification wherein a first monomer pre-soak of a monomer such as diethylaminomethacrylate followed by aqueous NVP present as the medium during gamma irradiation, results in a more stable, reproducible, hydrophilic surface for the highly flexible polysiloxane structure.

For PMMA substrates, the pre-soaking is preferably conducted at a temperature of from about 25° C. to about 80° C. for from about 0.5 to about 24 hours or more (up to about 48 hours) using a first aqueous solution containing from about 5% to about 50%, by weight, of monomer(s) to achieve optimum diffusion thereof into the PMMA substrate.

Where the substrate surface is polypropylene (PP), polyvinylidene fluoride (PVDF), a polycarbonate (PC), a polysulfone (PSF) or a polysiloxane (PDMSO), the surface is preferably pre-soaked in the monomer(s) or a first aqueous solution containing from about 5% to about 95%, by weight, of monomer(s), at a temperature of from about 25° to about 90° C., and for from about 0.5 to about 24 hours or more (up to about 48 hours), to achieve maximum and optimum diffusion of the monomer(s) into the substrate surface.

Where mixtures of NVP and HEMA are employed to form graft copolymerized coatings of P(NVP-HEMA), the mixtures may contain up to about 50%, by weight, of HEMA, based on the weight of the monomer mixture. However, above 20–30% HEMA, radical scavengers, and low monomer concentrations should be used to prevent gelation since HEMA enhances the onset of gelation.

It will be understood by those skilled in the art that the PVP, P(NVP-HEMA) or PHEMA graft coatings of this invention may be modified by copolymerization with various ionic monomers including use of such monomers for the pre-soak step. Mixtures of non-ionic hydrophilic monomers and ionic monomers may also be copolymerized therewith. For example, graft copolymerization incorporating vinylsulfonic acid, styrene sulfonic acid, sulfoethylmethacrylate, sulfopropylmethacrylate, or other vinyl sulfonic acids or vinylcarboxylic acids such as acrylic acid, crotonic acid or methacrylic acid can afford surface modifications which are anionic. Similarly, graft copolymerization incorporating basic or amino-functional monomers, e.g., vinylpyridines, aminostyrenes, aminoacrylates, or aminomethacrylates such as dimethylaminoethylmethacrylate, or dimethylaminostyrenes afford surface modifications which are cationic. It is also useful to use salts of ionic monomers or to convert ionic grafts to the salt form by post-treatment.

Amounts of ionic monomers up to about 50 wt. % of the total monomer weight may be employed, it being understood that the critical process parameters listed above may be maintained.

It will also be understood by those skilled in the art that the ocular implants to be graft coated may be also constructed of materials other than PMMA, PP, PVDF, PC, PSF or PDMSO to facilitate their use. It will be understood by those skilled in the art that such materials may be also be at least partially graft polymer surface modified so as to improve their properties as implant materials.

The hydrophilic graft polymer surface modifications of this invention are especially advantageous for intraocular lenses (anterior chamber, posterior chamber, and phakic) but are also of great value in affording improved tissue protection and improved biocompatibility for other ocular implants, such as corneal inlays, keratoprostheses, epikeratophakia devices, glaucoma drains, retinal staples, scleral buckles, etc.

Based on the foregoing considerations and the many process studies conducted, preferred conditions for various ocular article substrate polymers by way of example are provided in the examples below.

In general, choice of the "best" process will depend upon molecular structure of the substrate and grafting polymer, and the coating thickness desired. In general, those conditions which produce extreme solution viscosities and gels or conditions which could produce solvent stress cracking or crazing of the IOL polymers should be avoided. By way of example, the following process conditions are representative of practical conditions for the preparation of improved PVP grafts on various IOL polymer substrates according to this invention.

a) For PVP grafts on PP, PVDF and PDMSO, or combinations thereof, pre-soak the substrate in NVP monomer at 60° C. for 4 hours followed by graft polymerization in 10% aqueous NVP with about 0.15 Mrad gamma radiation at about 500 rads/min. dose rate.

b) For PVP grafts on PMMA, PP, PVDF and PDMSO, or combinations thereof, pre-soak the substrate in 40% aqueous NVP monomer at about 60° C. for 4 hours followed by graft polymerization in 10% aqueous NVP with about 0.15 Mrad gamma radiation at about 500 rads/min. dose rate.

c) For PVP grafts on PMMA, PDMSO and PC, or combinations thereof, pre-soak the substrate in 40% aqueous NVP monomer at about 60° C. for 12 hours followed by graft polymerization in 10% aqueous NVP with about 0.15 Mrad gamma radiation at about 500 rads/min. dose rate.

All percentages expressed in the following nonlimiting examples are by weight unless otherwise stated.

All contact angles (C.A.) and other surface characterizations for gamma polymerization grafts, unless otherwise indicated, are for samples washed with water or water-alcohol at room temperature or elevated temperatures to remove soluble residual monomer and ungrafted polymer for the improved surface graft processes of this invention. The resulting graft polymers are stable and permanent for long-term ocular implants and are not dissolved by aqueous media.

It will also be understood by those skilled in the art that the ocular implants to be graft coated may be also constructed of materials other than PMMA, PP, PVDF, PC or PDMSO to facilitate their use. It will be understood by those skilled in the art that such materials may also be at least partially graft polymer surface modified so as to improve their properties as implant materials.

The hydrophilic graft polymer surface modifications of this invention are especially advantageous for intraocular lenses (anterior chamber, posterior chamber, and phakic) but are also of great value in affording improved tissue protection and improved biocompatibility for other ocular implants, such as corneal inlays, keratoprosthesis, epikeratophakia devices, glaucoma drains, retinal staples, scleral buckles, etc.

EXAMPLE 1

This example illustrates the important effects which result from varying the above-discussed process conditions and polymerization parameters for gamma-irradiated polymer graft surface modification of PMMA with PVP.

PMMA slab samples were washed twice each by soap solution and distilled water using a sonicator. After complete drying the samples were put into NVP solutions in glass vials. The samples were then $\tau$-irradiated at various conditions. After $\tau$-irradiation, the surface modified PMMA samples were rinsed several times with $H_2O$ and evaluated.

The polymerized NVP grafting solutions or gels were freeze-dried under a vacuum. The solution PVP samples were evaluated for molecular weight by viscosity measurement ($M_v$) or gel permeation chromatography ($M_w$). For $M_v$, PVP was dissolved in distilled water and intrinsic viscosity $[\eta]$, was measured at 30° C. in a capillary viscometer.

PVP grafted PMMA samples were evaluated by water drop or underwater air bubble contact angle measurements. The bubble technique is regarded as more reliable for very hydrophilic surfaces. For air bubble C.A., the grafted PMMA was held horizontally in distilled water. An approximately 0.8 μl air bubble was formed and positioned underneath the test surface. Angles on opposite sides of the bubble were measured assuring symmetry. Five measurements were usually made for each sample. The results are set forth in the following tables:

TABLE 1

Dose Rate Effect on Solution Polymer Molecular Weight For $\tau$-Polymerized NVP
Concentration: 10% NVP in $H_2O$
Total Dose: 0.1 Mrads

| Distance from $CO^{60}$ source | Dose Rate (rads/min) | Time (hrs.min) | $[\eta]$ | Mol. Wt. ($M_v$) ($\times 10^6$) |
|---|---|---|---|---|
| 2" | 1235 | 1.21 | 1.48 | 1.15 |
| 4" | 309 | 5.24 | 2.21 | 2.27 |
| 6" | 137 | 12.09 | 2.61 | 3.04 |
| 8" | 77 | 21.36 | 2.85 | 3.49 |
| 10" | 49 | 33.45 | 3.56 | 5.09 |

The effect of dose rate was evaluated by PVP solution viscosity measurements. These results show that the molecular weight increased as dose rate decreased due to the slower and reduced initiation of radicals and the increased time of polymerization while maintaining the same total absorbed dose. At the lowest dose rate in this experiment, 49 rads/min (at 10" from the Cobalt-60 gamma source) the highest molecular weight PVP polymer, $M_v = 5.09 \times 10^6$, was obtained.

TABLE 2

Total Dose Effect on Molecular Weight
τ-Polymerized NVP
Concentration: 10% NVP in H₂O
Dose Rate: 309 rads/min (4" from τ-source)

| Total Dose (Mrads) | Time (hrs.min) | [η] | Mol. Wt. $M_v$ (× 10⁶) |
|---|---|---|---|
| 0.05 | 2.42 | 1.86 | 1.69 |
| 0.10 | 5.24 | 2.21 | 2.27 |
| 0.25 | 13.30 | * | — |
| 0.50 | 27.00 | * | — |

*Polymer solution gelled.

Table 2 shows the effect of total τ-irradiation dose on molecular weight at 309 rads/min. Increasing the total dose gives a higher molecular weight. A polymer gel was formed at a dose of 0.25 Mrad and higher. These results show that high irradiation dose can cause gelation or crosslinking of the PVP polymer.

TABLE 3

Molecular Weight of τ-Polymerized NVP at
Different Solution Concentrations
Total Dose: 0.1 Mrads
Dose Rate: 309 rads/min.
τ-Irradiation time: 5 hrs. 24 mins.

| NVP Concentration (%) | [η] | Mol. Wt. $(M_v)$ (× 10⁶) |
|---|---|---|
| 3 | 0.97 | 0.56 |
| 6 | 1.58 | 1.29 |
| 10 | 1.94 | 1.82 |
| 15 | 2.45 | 2.70 |

These results show the relation between the concentration of NVP monomer and the molecular weights of PVP at constant dose and dose rate. The results indicate that higher NVP concentrations give higher molecular weight polymers. The importance of dose rate is also indicated by the fact that even at 15% NVP, the PVP molecular weight ($M_v$) was only 2.7×10⁶ at 309 rads/min. compared to 5.0×10⁶ at a lower dose rate of 49 rads/min.

TABLE 4

Contact Angle of PVP τ-Grafted PMMA
at Different Dose Rates
Concentration: 10% NVP
Total dose: 0.1 Mrad

| Distance from τ-source | Dose Rate (rads/min) | Time (hrs.min) | Contact Angle |
|---|---|---|---|
| Ungrafted PMMA control | — | — | 65° |
| PVP Grafted PMMA | | | |
| 2" | 1235 | 1.21 | 31° |
| 4" | 309 | 5.24 | 24° |
| 6" | 137 | 12.09 | 21° |
| 8" | 77 | 21.36 | 19° |
| 10" | 49 | 33.45 | 15° |

The results in Table 4 show that the contact angles for PVP grafted PMMA decreased due to hydrophilic PVP grafting and that the lower dose rates give lower contact angles.

TABLE 5

Contact Angle of PVP τ-Grafted PMMA
at Different Total Doses
Concentration: 10% NVP in H₂O
Dose Rate: 309 rads/min.

| Total Dose (Mrad) | Contact Angle |
|---|---|
| Ungrafted PMMA Control | 65° |
| Grafted PMMA | |
| 0.05 | 27° |
| 0.10 | 25° |
| 0.25* | 24° |
| 0.50* | 24° |

*Polymer solution gelled.

These results show the effect of total dose on the contact angles of PVP τ-grafted PMMA. The contact angle showed little change above 0.05 Mrad at constant dose rate of 309 rads/min.

TABLE 6

Contact Angle of PVP τ-Grafted PMMA
at Different Monomer Concentrations
Total Dose: 0.1 Mrad
Dose Rate: 309 rads/min.

| NVP Concentration (%) | Contact Angle |
|---|---|
| Ungrafted PMMA Control | 65° |
| Grafted PMMA | |
| 3 | 29° |
| 6 | 27° |
| 10 | 25° |
| 15 | 21° |

The effect of different monomer concentrations was evaluated for PVP τ-grafts on PMMA by contact angle measurement. Even at 3% NVP and 0.1 Mrad, a major increase in hydrophilicity was observed as compared with non-grafted PMMA. The contact angle decreased slightly at monomer concentrations above 3%.

TABLE 7

Molecular weight of τ-Polymerized PVP
at Different Monomer Concentrations
Total Dose: 0.1 Mrad
Dose Rate: 64 rads/min.

| NVP Concentration (%) | [η] | Mol. Wt. $(M_v)$ (× 10⁶) |
|---|---|---|
| 1 | 0.79 | 0.40 |
| 3 | 1.65 | 1.38 |
| 5 | 2.23 | 2.30 |
| 10 | 3.35 | 4.59 |

These results show the relationship between the concentration of NVP monomer and molecular weight of PVP at a dose rate of 64 rads/min.

The molecular weight of PVP increases significantly with increasing concentration of NVP monomer.

TABLE 8

Contact Angle of PVP τ-Grafted PMMA
at Different Monomer Concentrations
Total Dose: 0.1 Mrad
Dose Rate: 64 rads/min.

| NVP Concentration (%) | Mol. Wt. $(M_v)$ (× 10⁶) |
|---|---|
| Ungrafted PMMA Control | 65° |
| Grafted PMMA | |
| 0 | 62° |
| 1 | 49° |
| 3 | 43° |
| 5 | 31° |

TABLE 8-continued

Contact Angle of PVP τ-Grafted PMMA
at Different Monomer Concentrations
Total Dose: 0.1 Mrad
Dose Rate: 64 rads/min.

| NVP Concentration (%) | Mol. Wt. ($M_v$) ($\times 10^6$) |
|---|---|
| 10 | 18° |

The contact angle of PMMA was evaluated after τ-grafting with NVP at different solution concentrations at a dose rate of 64 rads/min. These results show that the contact angles of PVP-grafted PMMA decreased with increasing concentration of NVP monomer. This result, at 64 rads/min dose rate is qualitatively similar to results at 309 rads/min (Table 6). Hydrophilicity at 10% monomer appears to be favored somewhat by the lower dose rate (C.A. 18° vs. 25°).

Polar organic solvents or aqueous-polar organic solvent mixtures may be useful for hydrophilic monomer graft polymerization. Typical of such organic solvents are alcohols or ethers such as methanol, ethylene glycol, polyethylene glycols, dioxane, etc. However, when such organic solvents act as radical traps or radical chain transfer agents, they must be used at concentrations lower than 50% or with high hydrophilic monomer concentrations (i.e., >25%). For example, methanol has some radical scavenger properties but may be used for PVP gamma grafts on PMMA in water-methanol mixtures up to 50-60% methanol for PVP grafts on PMMA using 0.1 Mrad and 10% monomer (Table 9). Hydrophilic grafts result although radical chain transfer by methanol appears to require low dose rates at 10% monomer. In general, these systems yield low viscosity solutions indicative of low molecular weight solution polymer which forms in the presence of radical inhibitors.

TABLE 9

Contact Angle of PVP τ-Grafted PMMA at Different
Dose Rates in 50% Methanol (MeOH) Solution
Concentration: 10% NVP in 50% MeOH
Total Dose: 0.1 Mrad

| Dose Rate (rads/min) | Contact Angle |
|---|---|
| No graft | 65° |
| 1065 | 36° |
| 326 | 28° |
| 157 | 27° |
| 64 | 20° |

EXAMPLE 2

This example illustrates the effect of swelling solvents on the surface modification process.

For hydrophilic gamma grafts on PMMA as the substrate, for example, addition of the swelling solvent, ethyl acetate (EtOAc), to aqueous monomer solutions is advantageous to achieve more efficient diffusion of monomer into the PMMA surface. Although EtOAc is not very soluble in water, a homogenous reaction medium can be achieved in the presence of a monomer such as NVP.

The thickness of the graft polymer surface modification can be increased by higher ethyl acetate concentrations and by longer diffusion times prior to irradiation; i.e., the time of pre-swelling. In general, without oxygen degassing, gamma radiation doses of 0.1-0.15 Mrad are suitable to achieve significant amounts of grafting.

The NVP-ethyl acetate-water solvent system is also a solvent for PVP and keeps the solution polymer phase homogenous.

"Embedded grafting" of PVP into the PMMA surface is made possible by irradiating the PMMA after exposure for various times to the monomer-swelling solvent-water mixture.

In experiments using these process techniques, samples were cleaned by sonication in a 10% soap solution followed by washing with distilled water. Prior to surface modification, PMMA samples were dried for 18 hours in a vacuum desiccator and weighed. NVP monomer was purified by vacuum distillation and stored at 4° C.

For gamma radiation grafting, the PMMA substrate was immersed in aqueous monomer-solvent solutions and exposed to gamma radiation. Typically, cleaned substrates were immersed in NVP-ethyl acetate-$H_2$ mixtures and irradiated in a 600 Curie Co-60 source. The samples were exposed to the monomer solution for various lengths of time. Gamma doses ranging from 0.01-0.15 Mrad as measured by Fricke dosimetry were used in this experiment. Dose rates were also varied. After irradiation, samples were removed from the gamma polymer solution and washed several times with distilled water and in deionized water with agitation. Some samples were weighed hydrated after blotting with filter paper to remove surface water and then dried for 24 hours in a vacuum desiccator. The polymerization solutions ranged from clear viscous solutions to gels. The following parameters were measured.

One measure of the degree of grafting was obtained from the weight increase of the substrate according to the following equation:

$$\text{percent grafting} = \frac{W_1 - W_o}{W_o} \times 100$$

where $W_o$ is the initial weight of PMMA and $W_1$ is the weight of grafted PMMA. Likewise, percent hydration was calculated according to the following equation:

$$\text{percent hydration} = \frac{W_w - W_d}{W_d} \times 100$$

where $W_w$ is the weight of PMMA after equilibration in water (after blotting it dry) and $W_d$ is the weight of dry sample (after desiccation). In most cases, the maximum water uptake was reached after 12 hours.

Captive air bubble and n-octane contact angles were measured for the radiation grafted PMMA surfaces to estimate the hydrophilicity of modified surfaces. Static contact angles were measured on a Rame-Hart contact angle goniometer. At least five measurements on different surface regions of each sample were made.

IR/ATR surface analysis of the grafted and ungrafted surfaces was made by using a Perkin-Elmer Model 283B IR Spectrometer using attenuated total reflectance.

Samples of 1 $cm^2$ grafted and ungrafted PMMA were analyzed using a Kratos ES 300 ESCA spectrometer employing a magnesium Kα x-ray source. Graft analysis consisted of N/C ratio determination.

The molecular weights of PVP solution polymers were determined by solution intrinsic viscosity measurements at 30° C. in a Ubbelhode viscometer.

Radiation doses ranged from 0.01 to 0.15 Mrad and monomer concentrations ranged from 5 to 15%.

Data for PVP grafting onto PMMA using EtOAc as a swelling solvent are shown in Table 10. Since no pre-radiation swelling time is used here, diffusion penetration of the surface by EtOAc and monomer occurs during gamma radiation. Some pre-radiation swell-time is considered preferable. This system exhibits behavior typical of a reaction which involves monomer diffusion control. Partitioning of NVP monomer into the hydrophobic surface of PMMA is favored initially because of the presence of the ethyl acetate, which is a swelling solvent for PMMA.

By the use of a swelling solvent for the graft substrate (i.e., EtOAc), the NVP-EtOAc-$H_2$ system swells the surface layers of PMMA and polymerization grafting of monomer molecules in the vicinity of radiation induced radical species near the surface is immediate. Under such conditions, more efficient grafting is achieved at lower doses and with deeper penetration of the graft polymer into the solvent swollen surface.

Measurement of percent swelling of PMMA samples in NVP-ethyl acetate-$H_2O$ (1:1:8) vs. time shows that swelling of about 6% is attained after 12 hours. In this system, the thickness of the grafted layer could be controlled by changing the time allowed for diffusion prior to irradiation, thus controlling the thickness of the grafted zone. Table 11 shows the graft behavior after 24 hours of pre-swelling of PMMA in 1:9 ethyl acetate:water containing 15% of NVP. Comparing this data with Table 10 (no swelling time), it is clear that the % graft is significantly higher for pre-swelling PMMA. At a given ethyl acetate concentration, this difference is generally more pronounced at lower monomer concentrations, e.g., 5% monomer compared to 15% monomer.

In this system, NVP is the monomer but also acts as a mutual solvent to maintain a homogeneous phase of otherwise poorly miscible solvents, i.e., ethyl acetate and water. At a given monomer concentration (e.g., 10%), it is necessary to keep the concentration of ethyl acetate below 10% to avoid phase separation to a micro-emulsion. Variation of the ethyl acetate concentration, being a swelling agent, affects graft yield. Table 12 summarizes the observations made by varying the concentration of ethyl acetate while keeping other factors constant showing that the percent grafting does increase with higher ethyl acetate concentrations. Greater grafting efficiency is also indicated by the significant % grafting and reduction of C.A. in the solvent swelling monomer system at low doses. For example, up to 0.05 Mrad, little grafting occurs in a simple aqueous monomer system. In contrast, at only 0.01 Mrad C.A. is reduced to 35° (Table 11, 24 hr. pre-swell) and to 23° at 0.03 Mrad.

Techniques used for the chemical analysis of bulk polymers are usually not very satisfactory for analysis of the surfaces of polymers. The surface region, which is significantly different in structure and/or chemistry from the bulk, is present only as a fraction of the mass of the polymer. Thus, the traditional techniques of chemical analysis are inadequate. Special surface analysis techniques are required for graft copolymers since the surface region is a complex mixture of graft, substrate, cross-linking groups and chain transfer products. Two spectroscopic methods, ATR-IR and ESCA, are the most useful methods now available for this purpose and were used to help characterize grafted surfaces.

The results for ATR-IR (attenuated total reflection infrared) shown in Table 13 indicate that the ration of C=O (ester) and C=O (amide) groups in the surface changes from 7.67 to 1.68 as the gamma dose increases from 0.01 to 0.10 Mrad and then levels off which is consistent with PVP grafting on PMMA.

ESCA analyses are shown in Table 14 and indicate increasing nitrogen composition with increasing dose (and grafting) as expected for a PVP graft.

Scanning electron microscopic examinations of the grafted samples were performed in order to observe their surface morphologies. All of the coated surfaces appeared smooth even at 10,000×. The graft polymer surface modifications appear to provide uniform coverage across the surface of PMMA substrate. This is important to ensure excellent retention of optical properties for an optical implant such as an intraocular lens.

Major conclusions to be drawn from the results of this example are:

The NVP-ethyl acetate-water system produces uniform hydrophilic graft polymer surfaces with controllable graft penetration using PMMA as the substrate.

The monomer-ethyl acetate-water grafting front gradually penetrates into the substrate and may be controlled by varying the concentration of swelling agent and the time of pre-swelling.

The presence of the PVP surface graft was confirmed by gravimetric, contact angle, ATR-IR and ESCA measurements.

Unusually low radiation doses are required to achieve significant grafting. Hence, any possible radiation damage to the surface or substrate is minimized.

TABLE 10

Graft Polymerization of NVP on PMMA
Swelling time - 0 hours
Ethyl acetate: $H_2O$ (1:9)

| Dose Rate (rads/min) | NVP Conc. | 0.01 Mrad C.A. | 0.01 Mrad % Graft | 0.05 Mrad C.A. | 0.05 Mrad % Graft | 0.10 Mrad C.A. | 0.10 Mrad % Graft | 0.15 Mrad C.A. | 0.15 Mrad % Graft |
|---|---|---|---|---|---|---|---|---|---|
| 309 | 5% | 48 | — | 47 | 0.5 | 42 | 0.7 | 36 | 0.7 |
|  | 10% | 46 | 0.1 | 34 | 0.4 | 22 | — | 17 | 0.5 |
|  | 15% | 40 | 0.2 | 32 | 0.5 | 16 | 0.9 | 18 | 0.5 |
| 77 | 5% | 40 | 0.2 | 38 | 0.2 | 41 | 0.6 | 38 | 0.3 |
|  | 10% | 36 | 0.6 | 32 | 0.4 | 35 | 0.7 | 36 | 0.5 |
|  | 15% | 38 | 1.1 | 25 | 0.5 | 28 | 0.8 | 26 | 0.6 |

TABLE 11

Grafting of NVP on PMMA: 24 Hours Swelling
Solvent - 9:1/$H_2O$—EtOAc/NVP - 15%

| Total Dose (Mrads) | 309 rads/min C.A. | 309 rads/min % Graft | 77 rads/min C.A. | 77 rads/min % Graft |
|---|---|---|---|---|
| 0.01 | 38 | 1.0 | 35 | 1.3 |
| 0.03 | 27 | 2.3 | 23 | 2.8 |
| 0.05 | 17 | 2.5 | 17 | 2.4 |
| 0.10 | 16 | 3.0 | 16 | 3.2 |

TABLE 11-continued

Grafting of NVP on PMMA: 24 Hours Swelling
Solvent - 9:1/$H_2O$—EtOAc/NVP - 15%

| Total Dose (Mrads) | 309 rads/min | | 77 rads/min | |
|---|---|---|---|---|
| | C.A. | % Graft | C.A. | % Graft |
| 0.15 | 10 | 3.0 | 16 | 3.4 |

TABLE 12

Graft Polymerization of NVP on PMMA
Effect of Ethyl Acetate: 12 hours Swelling
10% NVP, 309 rads/min

| Total dose | 3% EtOAc | | 6% EtOAc | | 10% EtOAc | |
|---|---|---|---|---|---|---|
| (Mrads) | C.A. | % Graft | C.A. | % Graft | C.A. | % Graft |
| 0.01 | 43 | 0.2 | 44 | 0.4 | 48 | 0.6 |
| 0.03 | 38 | 0.3 | 26 | 0.5 | 25 | 1.7 |
| 0.05 | 23 | 0.3 | 21 | 0.5 | 22 | 1.9 |
| 0.10 | 18 | 0.5 | 17 | 0.5 | 18 | 2.2 |
| 0.15 | 15 | 0.5 | 17 | 0.6 | 18 | 2.2 |

TABLE 13

ATR-IR Spectral Analysis of PVP Grafted PMMA Samples*

| Total Dose (Mrad) | $V_c = 0$ (ester) / $V_c =$ (amide) |
|---|---|
| 0.01 | 7.67 |
| 0.03 | 6.51 |
| 0.07 | 4.61 |
| 0.10 | 1.68 |
| 0.15 | 1.66 |

*Reaction mixture 5% NVP in 9:1 mixture of water-ethyl acetate. dose rate 1065 rads/min - Swelling time: 17 hours.

TABLE 14

ESCA Analysis of PVP Grafted PMMA Samples*

| Total Dose (Mrad) | N/C at 0° C. |
|---|---|
| 0.03 | $2.2 \times 10^{-2}$ |
| 0.05 | $3.1 \times 10^{-2}$ |
| 0.07 | $4.5 \times 10^{-2}$ |
| 0.10 | $4.7 \times 10^{-2}$ |

*Reaction mixture 5% NVP in 9:1 mixture of water-ethyl acetate. Dose rate 1065 rads/min - Swelling time: 17 hours.

EXAMPLE 3

The following experiment demonstrates the very significant influence of oxygen on gamma polymerization and gamma grafting and the important beneficial effects of carrying out graft polymerizations in the substantial absence of oxygen.

Gamma radiation induced polymerization of NVP was carried out in 10% NVP aqueous solution as follows:
(a) polymerization in presence of oxygen (air);
(b) polymerization in absence of oxygen using argon degassing; and
(c) polymerization in absence of oxygen.

For Group (a), aqueous 10% NVP solutions were irradiated to total doses of 0.01, 0.05, 0.10, 0.20 and 0.25 Mrad in each case at 213 rads/min in the presence of air. An argon purge for 10 minutes was used in the case of Group (b). A vacuum freeze-thaw (FT) method was employed for degassing in the case of Group (c). In the freeze-thaw experiments, the monomer solution was frozen in liquid nitrogen and then vacuum (0.3 mm) was applied to eliminate oxygen. The frozen solution was thawed and brought to room temperature before irradiation. Some samples were subjected to three freeze-thaw cycles (3 FT). Experiments were run in duplicate to establish reproducibility.

To determine the oxygen degassing effects on gamma radiation grafting and polymerization, monomer conversions and molecular weights were determined for the different NVP solutions irradiated at 0.01 Mrad to 0.25 Mrad at 213 rads/min.

A method used for determining unreacted NVP after irradiation was as follows: 5 ml of the gamma irradiated NVP solution was extracted using 50 1 acetonitrile. NVP is soluble in acetonitrile but PVP is not. The PVP precipitate was centrifuged and the supernatant solution was analyzed for NVP. The NVP monomer solution (10% NVP/aqueous) was used as a control. NVP analysis was as follows: The 10% by weight aqueous solution was diluted with acetonitrile to appropriate concentrations (0.5 g/ml to 5.0 μg/ml). The U.V. absorbance was measured for each solution at 323 nm to develop a standard curve of NVP concentration vs. U.V. absorbance. The regression coefficient was 0.99 for this curve. GPC was used for molecular weight measurements and gives $M_w$ as well as molecular weight distribution.

The % NVP conversion (amount of monomer reacted) is significantly affected by Ar purge deoxygenation and by FT oxygen degassing. At the very low dose of 0.01 Mrad, virtually no polymerization occurs in the non-degassed oxygen (air) containing solutions. However, 46%, 61% and 63% conversion to PVP occurred for the AR-purged, 1 FT and 3 FT samples, respectively. Even at 0.10 Mrad, samples irradiated in air showed only 90% conversion (10% unreacted NVP monomer) compared to virtually complete conversion (99%) for oxygen degassed systems. This is important for biological implants where unreacted monomers can cause serious adverse toxicological behavior.

To demonstrate more efficient grafting of PVP on PMMA at low gamma doses in the oxygen degassed system, 10% aqueous NVP was argon purged to remove oxygen and irradiated with PMMA samples at 157 rads/min to 0.05 Mrad. The resulting hydrophilic surface modification had C.A. 20° and was stable (no change in C.A.) to mechanical abrasion. As indicated above, this mechanically stable and very hydrophilic graft of PVP on PMMA graft is achieved with high monomer conversion (98%) and a high degree of polymerization for the solution polymer ($1.65 \times 10^6$ mol. wt.). In the presence of air (oxygen), higher radiation doses (>0.1 Mrad) and/or higher monomer concentration (15% or more) are required to achieve low C.A. with high conversion and high molecular weight. For hydrophilic monomer gamma polymerization grafts on other substrate polymers, i.e., polypropylene, fluorocarbons (e.g., PTFE or PVDF) or silicones, the beneficial effect of oxygen degassing can be even greater. Oxygen removal may also be used for improved gamma grafting in combination with the use of substrate swelling solvents and free radical inhibiting agents such as oxidizable metal salts or organic compounds (e.g., ascorbic acid). In the presence of radical inhibitors effective grafting may be achieved, but solution polymer may be of low mol. wt.

PVP molecular weight is also greatly affected by oxygen degassing. The Ar-purged and FT samples yield PVP polymers with molecular weights of about $1.6 \times 10^6$ at only 0.01 Mrad. In sharp contrast, the non-degassed samples do not form high mol. wt. polymer. At 0.05 Mrad, oxygen degassed samples yield PVP with molecular weights of $1.65-1.8 \times 10^6$ compared with only about $0.35 \times 10^6$ in air. At 0.10 Mrad, all samples have molecular weights of about 1.8 to $2.0 \times 10^6$.

EXAMPLE 4

The following experiments were carried out to demonstrate the advantageous effects of free radical scavengers in inhibiting solution polymerization and gelation during the graft polymerization process, especially at high monomer concentrations.

PMMA samples were surface grafted with PVP using gamma irradiation as in Example 1. Ascorbic acid (AscA) was used as a radical inhibitor in these experiments. The irradiation conditions are set forth in Table 15.

TABLE 15

(a) 30% NVP/0.5 mM AscA/2.5% EtoAc/0.2 Mrad*
(b) 30% NVP/0.5 mM AscA/2.5% EtoAc/0.15 Mrad
(c) 40% NVP/1.0 mM AscA/0.1 Mrad
(a) 50% NVP/1.0 mM AscA/0.1 Mrad
(e) 50% NVP/1.0 mM AscA/0.2 Mrad*

*0.1 Mrad initial dose; additional 0.1 Mrad after washing sample free of monomer and soluble polymer.

C.A. for all PMMA samples in Table 15 were 18°–24° indicating very high hydrophilic grafts. Dose rates used were 33 rads/min. A dose rate of 667 rads/min for (b) was also used. Solution polymer gelation can occur under these conditions at these monomer concentrations (30–50%) if a radical inhibitor such as AscA is not used. The AscA significantly inhibits solution polymerization without interfering with grafting yielding low mol. wt. solution polymer. In addition to C.A., PVP grafting was verified by ESCA and FTIR-ATR analysis showing the presence of surface nitrogen and the PVP imide carbonyl group. Good mechanical properties were demonstrated by an abrasion test showing little change in C.A. or surface nitrogen after abrasion.

EXAMPLE 5

This example demonstrates the large favorable effect of hydrophilic gamma graft surface modification on reducing tissue adhesion by measuring corneal endothelium adhesion, and cell adhesion using fibroblast cells. These are important factors in demonstrating the improved biocompatibility and minimal tissue irritation or damage afforded by the hydrophilic graft surface modifications of this invention.

An apparatus which measures the force of adhesion ($mg/cm^2$) between contacting polymer and tissue surface was used to determine adhesion between rabbit corneal endothelium and polymer surfaces. Adhesion force values of about 250–400 $mg/cm^2$ were measured for PMMA and other hydrophobic polymers evaluated for implants, i.e., silicone, polypropylene, etc. The improved hydrophilic gamma graft surfaces, prepared under preferred process conditions, exhibit much lower adhesion; below 150 $mg/cm^2$ and often less than 100 $mg/cm^2$. This is accompanied by a major reduction in endothelium cell damage as measured by SEM; from about 50–80% damage for PMMA or silicone to 20% or less for surfaces gamma grafted under preferred process conditions of this invention.

The gamma graft surface modifications of this invention also show a major reduction in cell adhesion as demonstrated by exposure to live cell cultures of chick embryo fibroblast cells (CEF) or rabbit lens epithelial cells (LE). Experiments indicate that 2–4 times more CEF or LE cells adhere to PMMA as compared to PVP graft modified PMMA. Grafts prepared at 0.1 Mrad and using 15% NVP, for example, showed adherence of only 35% of the number of CEF cells which adhere to PMMA. Similarly, PHEMA grafts on PMMA exhibited only 38% cell adhesion and 15:1 NVP:HEMA (at 16% total monomer) exhibited only 20% CEF cell adhesion compared to PMMA. Under optimal conditions of the method of the invention for PVP surface modified PMMA, PC or PDMSO, less than 1–2 LE cells per sq. mm. adhere as compared to about 10 LE cells or more to unmodified PMMA, PC or PDMSO.

EXAMPLE 6

This example demonstrates the graft polymerization of HEMA and mixtures of NVP and HEMA on PMMA.

The method of Example 1 was repeated utilizing a 16% NVP/HEMA (15:1) aqueous solution at about 1300 rads/min and 0.10 Mrad dose. The PVP-PHEMA surface modified PMMA had a C.A. of 17°. Under similar conditions, a 7% NVP/HEMA solution (5:2) gave a surface with C.A. 23°, and a 2.5% HEMA solution gave a surface with C.A. 18°.

EXAMPLE 7

This example demonstrates the graft copolymerization of anionic or cationic monomers with the hydrophilic monomers of this invention using ionic monomers with NVP.

a. The method of Example 1 was used with PMMA substrate and 15% NVP plus 1–5 wt % of acrylic acid (AA) or crotonic acid (CA) as comonomers at 0.1 Mrad and 1235 rads/min. Contact angles were 18°–22° and endothelium adhesion was about one-half or less that of unmodified PMMA indicating formation of a good hydrophilic graft coating. Similar results can be obtained using dimethylaminoethylacrylate to produce cationic graft coatings. Styrene sulfonic acid (SSA) was also used to produce anionic grafts with NVP on PMMA according to the method of Example 1. Using an SSA:NVP ratio of 1:2 (33% SSA) and total monomer concentration of 30% at 0.15 Mrad and about 700 rads/min dose rate, hydrophilic grafts with 30°–40° C.A. were prepared.

b. Styrene sulfonic acid sodium salt (NaSSA) was used to prepare highly hydrophilic anionic copolymer grafts with NVP on silicones (PDMS). PDMS samples were cleaned by sonication in ethanol and vacuum dried prior to irradiation in aqueous monomer solutions. Table 16 lists grafting conditions, monomer concentrations, and contact angles for graft surfaces prepared at a dose rate of about 700 rads/min.

TABLE 16

| Dose (Mrad) | % NaSSA | % NVP | C.A. |
|---|---|---|---|
| 0.05 | 20 | 20 | 17° |
| 0.10 | 20 | 20 | 15° |
| 0.15 | 20 | 20 | 13° |

As shown in Table 16, under conditions of even a relatively low total dose of 0.05 Mrad, using 40% total monomer and 50% anionic NaSSA comonomer with NVP, very hydrophilic (C.A. 17°) anionic grafts were achieved.

EXAMPLE 8

This example demonstrates the hydrophilic monomer surface grafting of polypropylene (PP) and the importance of oxygen degassing for effective surface modification.

Hydrophilic surface grafts on polypropylene are not readily prepared by gamma irradiation of aqueous NVP in the presence of oxygen. Under conditions of Example 1, even at gamma doses >0.1 Mrad and monomer concentrations >10%, little surface hydrophilicity and little reduction in C.A. occurs. However, in oxygen degassed media, at 157 rad/min and doses as low as 0.01-0.05 Mrad with 10% NVP, contact angles were about 15°. Very hydrophilic PP grafts which are also mechanically stable by a mechanical abrasion test are thereby readily prepared using oxygen degassed process conditions. This is especially important for gamma graft surface modification of IOLs with PMMA optics and PP haptics.

EXAMPLE 9

Polycarbonate is a useful engineering plastic for ocular implants. Surface modification of polycarbonate is most readily accomplished using gamma radiation of oxygen degassed aqueous monomer NVP solutions, e.g., grafting conditions of oxygen degassed 10% NVP at 93 rad/min and 0.05 Mrad dose yield C.A. 19°.

EXAMPLE 10

Although silicone (PDMSO) does not gamma graft with NVP as readily as PMMA, PDMSO surfaces were modified using oxygen degassed 10% NVP solutions. Irradiation to 0.05 Mrad at 93 rad/min yields C.A. of about 45° indicating significant surface hydrophilicity. Higher doses, swelling solvents, higher monomer concentrations, and different hydrophilic monomers can produce improved hydrophilicity. For example, gamma grafting of NVP/HEMA (10:1) at 0.10 Mrad and 157 rad/min even without oxygen degassing yields grafts with 30° C.A.

EXAMPLE 11

Polyvinylidene fluoride (PVDF) is an example of a fluorocarbon polymer which can be surface modified by gamma irradiation of aqueous NVP, NVP/water-methanol solutions or EtOAc-water systems. Hydrophilic grafts, with C.A. about 30°, are prepared at 326 rad/min and 0.20 Mrad. However, PVDF is preferably grafted using oxygen degassed process conditions. Conditions of 157 rad/min, 0.05 Mrad and 10% aqueous NV produce PVP grafts with C.A. 17°. Since NVP monomer is also an effective swelling solvent for PVDF, allowing pre-radiation swelling time is favorable for producing improved grafts. For example, C.A. as low as 14° is obtained using 5 hrs. swelling time with 7% NVP, 0.1 Mrad and 94 rads/min.

EXAMPLE 12

Grafting Conditions for Combinations of Materials: Lenses with Haptics of Different Polymers One of the important aspects of this invention is the discovery that certain specific grafting process conditions make it feasible to surface modify combinations of materials to be used as lens/haptic pairs in ocular implants. Surface grafting of an assembled IOL can then take place in a one-step simultaneous gamma or electron beam irradiation grafting procedure yielding improved, more biocompatible surfaces. Lens materials such as PMMA, PC and PDMSO can thereby be grafted under specific conditions of this invention which also achieve good grafting of haptic fiber materials such as PVDF or PP. Table 17 summarizes some lens/haptic combinations with preferred mutual grafting conditions for obtaining improved PVP grafts.

PMMA/PP and PMMA/PVDF

It has been demonstrated that PMMA and PP gamma graft under degassed conditions at 157 rad/min, 0.05 Mrad, 10% NVP. These conditions yield contact angles of 20° and 15° for PMMA and PP, respectively, and are mechanically stable. Non-degassed PP does not graft efficiently under conditions similar to PMMA because of the adverse effect oxygen has on PP surface grafting.

PVDF surface graft studies also indicate the importance of oxygen degassing. A 10% degassed aqueous NVP solution, irradiated at 157 rad/min to 0.05 Mrad, gives good hydrophilic grafts on both PMMA and PVDF. See Table 17.

PC/PP and PC/PVDF

PC and PP graft under similar gamma irradiation conditions when NVP solutions are degassed. Using 157 rad/min, 0.05 Mrad and 10% aqueous NVP solutions, efficient hydrophilic grafting occurs on both polymers yielding contact angles of 19° and 15°, respectively.

PVDF and PC are both grafted under the same conditions which graft PC/PP and PMMA/PP combinations; e.g., 157 rad/min, 0.05 Mrad, 10% degassed NVP. Since PVDF swells in NVP, gamma grafting with prior swelling time can result in improved binding of PVP to the PVDF. Conditions are thereby afforded for simultaneous hydrophilic polymer grafting to IOLs, or other ocular implants which are made of two or more polymers as indicated above. See Table 17.

TABLE 17

| Surface Modification of Lens/Haptic Combination with PVP | |
|---|---|
| Lens/Haptic | Typical Preferred Gamma Polymerization Grafting Conditions* |
| PMMA/PP | a. 10% degassed NVP, low dose rate (LDR)**, 0.05 Mrad. |
| | b. 2.5% EtOAc, 6 hr swell. 10% NVP, degassed LDR, 0.05 Mrad. |
| PMMA/PVDF | a. 10% degassed NVP, LDR, 0.05 Mrad. |
| | b. 10% NVP, 5 hr swell, LDR, degassed, 0.15 Mrad. |
| | c. 2.5% EtOAc, 6 hr swell, 10% NVP degassed, LDR, 0.05 Mrad. |
| PC/PP | a. 10% degassed NVP, LDR, 0.05 Mrad. |
| | b. 2.5%, EtOAc, 6 hr swell, 10% NVP, LDR, degassed. |
| PC/PVDF | a. 10% degassed NVP, LDR, 0.05 Mrad. |
| | b. 10% NVP, 5 hr swell, LDR, degassed, 0.05 Mrad. |
| | c. 2.5% EtOAc, 6 hr swell, 10% NVP, degassed, LDR, 0.05 Mrad. |

*To produce C.A. less than about 25°.
**LDR: 30-300 rads/min.

EXAMPLE 13

This example illustrates the efficient grafting which can be achieved by the process of this invention at extremely low gamma doses (0.005 Mrad or less) even at very low aqueous monomer concentrations (0.5 wt % or less).

PVDF surfaces were surface modified using conditions described in the above examples at the extremely low gamma-radiation doses (0.01 and 0.005 Mrad) and low HEMA monomer concentrations (0.5-2.0%) summarized in Table 18. PVDF samples were cleaned, gamma irradiated in aqueous HEMA solutions and washed according to the general method of Example 1. Highly hydrophilic surface graft modifications are achieved as indicated by the low contact angles listed in Table 18. Good graft efficiency for PHEMA on PVDF under these extremely low dose and low monomer concentration conditions is further confirmed by the XPS analyses given in Table 19 which shows little surface fluorine and a corresponding increase in carbon for the PHEMA-g-PVDF; a surface analysis which closely approximates the composition of PHEMA.

TABLE 18

Gamma Radiation Graft Polymerization of Argon Degassed Aqueous HEMA on PVDF at 88 rads/min

| Total Dose (Mrads) | % HEMA | Contact Angle (°) |
|---|---|---|
|  | 0.5 | 24 |
| 0.005 | 1.0 | 24 |
|  | 2.0 | 12 |
|  | 0.5 | 21 |
| 0.01 | 1.0 | 19 |
|  | 2.0 | 16 |

Even at doses as low as 0.005 Mrad or less and monomer concentrations as low as 0.5 wt % of less, extremely hydrophilic PHEMA grafts are obtained. For comparison, PVDF itself is very hydrophobic and has a contact angle greater than 85°.

TABLE 19

| XPS Analysis of PVDF and PHEMA-g-PVDF | | |
|---|---|---|
|  | C (1s) Carbon | F (1s) Fluorine |
| Unmodified PVDF | 50.5 | 45.3 |
| PHEMA-g-PVDF 2% HEMA 0.005 Mrad | 69.0 | 0.9 |
| PVDF (theoretical) | 50.0 | 50.0 |
| PHEMA (theoretical) | 66.7 | — |

The XPS surface analysis clearly shows that efficient surface grafting of PHEMA occurred at 0.005 Mrad. The surface carbon concentration for the graft was about that expected for a PHEMA surface and very little surface fluorine for PVDF was detected.

EXAMPLE 14

The following demonstrates the enhancement of the above-described methods achieved by pre-soaking the polymer surface in a first solution of the monomer prior to graft polymerizing the monomer thereon from a second solution of the monomer.

All substrates were cleaned by ultra-sonication in a 0.1% aqueous Triton X solution for 20 minutes and then thoroughly rinsed with hot (60° C.) distilled water. After drying in vacuum, the samples were stored in a desiccator until use.

The incorporation of monomer into the substrate by pre-soaking in monomer or aqueous monomer solutions at room temperature or elevated temperatures was found to be surprisingly simple and effective to facilitate the diffusion of monomer into the substrate to yield improved, thicker and more readily controlled grafted surface modifications. Several practical conditions for this improved method are noted as follows by way of example:

Method A: Pre-soak in 100% NVP at 25° C. or 60° C. for 4-24 hours.

This method was used for PDMSO, PP, PVDF, polyethylene and polyurethane. However, it is not preferred for PMMA because of potential stress cracking and/or crazing of PMMA induced by 100% NVP.

Method B: Pre-soak in 40% aqueous NVP at 25° C. or 60° C. for 4-48 hours.

This method was used for substrates PMMA, PDMSO, PP, PVDF, polyethylene, polyurethane and polyvinylchloride.

Method C: Pre-soak in 100% DMAEMA, 100% NVP, 50% DMAEMA/50% NVP, or 50% aqueous DMAEMA at 25° C. for 2-24 hours.

This method was useful for PDMSO, PMMA, PP and PVDF.

After pre-soak, samples (polymer slabs or lenses) were typically transferred to 10% aqueous NVP and vacuum or argon degassed. Gamma irradiation was carried out at room temperature in a Cobalt 60 source to a total dose of 0.15 Mrad. The dose rate used was 484 rad/min. Immediately after irradiation, samples were rinsed with warm water and then washed with repeated changes of distilled water for 4 days.

Gravimetric analysis: The initial dry substrate weight $W_o$ was obtained after drying in a vacuum oven at 60° C. for 12 hours. The pre-soak treatments in monomer or aqueous monomer solutions were performed at about 60° C. The extent of monomer or monomer/water absorbed by pre-soaking ($W_1$) was measured by weighing pre-soaked samples. The % uptake (% $W_m$) is given by:

$$\% \ W_m = (W_1 - W_o)/W_o \times 100$$

The radiation grafted samples were dried under vacuum at 60° C. for 12 hours. $W_2$ was the measured weight of the grafted sample and the extent of grafting. % $W_g$ was calculated as:

$$\% \ W_g = (W_2 - W_o)/W_o \times 100$$

Air bubble contact angles were measured under water to obtain wettability of the substrates and graft surfaces. Contact angles usually for six bubbles measured on both sides of a sample were averaged. The measurements were done on a Rame-Hart contact angle Goniometer.

FTIR/ATR spectra were obtained using a Nicolet 60SX spectrometer equipped with an MCT detector. The ATR stage was a Barnes variable angle and was set at 45°. Samples (1×1 cm$^2$) were pressed against a KRS-5 crystal. In order to maintain the uniform contact, samples were clamped against the crystal with a torque wrench in 5 in. lbs. Typically 200 scans were averaged for the ATR experiments. All spectral manipulations were done with standard Nicolet computer software.

An effective method for staining PVP grafts using alcoholic eosin was reported by Yasuda [Yasuda et al, J.

Polym. Sci., Part A., Vol. 2, p. 5093 (1964)]. Because alcohol crazes some substrates, an eosin solution in acetic acid was used. PVP-g-PDMSO samples were stained overnight, then removed and soaked in water for 12 hours to remove any non-bonded stain. The homogeneity and intensity of color gave qualitative information on the PVP graft and also quantitative information on the graft thickness by optical microscopy. PVP-g-PMMA was examined without staining. The contrast between graft layers and bulk were very distinguishable for grafts thicker than 3-5 microns.

It has been difficult in the prior art to minimize solution homopolymerization to avoid excessively high solution viscosities for the graft polymer solutions, especially for achieving good, uniform, optically clear, thicker grafts (to 150 microns or more). Solution homopolymerization to very high molecular weight, particularly under conditions suitable for thicker grafts, makes sample removal and washing difficult. The present invention provides a simple method which allows improved control over these parameters. The homopolymer molecular weight and solution viscosity can be low to permit easy removal and washing of the polymer solution with minimum handling.

To facilitate the diffusion of monomer into the polymer substrate, it is preferred to employ a combination of relatively high monomer soak concentrations (e.g., 40 and 100%) and/or elevated temperatures (e.g., 60° C.). All of the ocular implant substrate polymers used were found to readily incorporate the hydrophilic monomers, i.e., NVP (Tables 17 and 18). However, the extent of monomer uptake varies from one substrate to another as a function of molecular structural considerations, crystallinity, hydrophobicity, etc. (Tables 17 and 18). The monomer concentration also has a considerable effect on monomer uptake and eventually on grafting. Method B (40% aqueous NVP) generally shows less monomer uptake than Method A (100% NVP). Although the monomer or aqueous monomer pre-soak may be varied, a temperature of 60° C. is often convenient and results in greater polymer chain mobility and more rapid diffusion of monomer into the graft substrate than at lower temperatures without dimensional or structural distortion of the ocular implant.

Improved grafting was obtained in all systems using the pre-irradiation monomer soak process as shown in Tables 20 and 21. There is often a correlation between the monomer uptake during pre-swelling and the amount of graft. These observations suggest that the monomer present in the subsurface and at the interface readily participates in the graft polymerization. Under the conditions of the method of the invention, the rate of monomer diffusion out of the polymer into the solution appears slower than the rate of the graft polymerization. Typical conditions for grafting after monomer or comonomer pre-soak are irradiation at 484 rads/min to 0.15 Mrad in 10% degassed NVP solution.

Air bubble contact angles for the modified surfaces are given in Tables 20 and 21. All contact angles were below 20° C., indicating highly hydrophilic PVP grafts on all substrates, PMMA, PP, PVDF and PDMSO.

TABLE 20

Grafting of PVP on Various Substrates by Method A
Pre-soak in 100% NVP at 60° C. for 4 hrs.,
Grafting in 10% NVP with 0.15 Mrad at 484 rad/min.

| Ocular Implant Polymer Substrate | % $W_m$ | % $W_g$ | % $W_g$ No Pre-soak | Air Bubble Contact Angle |
|---|---|---|---|---|
| PDMSO | 7.6 | 5.3 | 0.5 | 18° |
| PP (Blue) | 5.7 | 3.9 | <0.1 | 18° |
| PP (Clear) | — | 3.7 | — | 18° |
| PVDF | 21.9 | 8.8 | 0.3 | 19° |

% $W_m$ = Wt % Monomer uptake
% $W_g$ = Wt % Graft

TABLE 21

Grafting of PVP on Various Substrates by Method B
Pre-soak in 40% NVP at 60° C. for 4 hrs.,
Grafting in 10% NVP with 0.15 Mrad at 484 rad/min.

| Ocular Implant Polymer Substrate | % $W_m$ | % $W_g$ | % $W_g$ No Pre-soak | Air Bubble Contact Angle |
|---|---|---|---|---|
| PDMSO | 1.9 | 1.0 | 0.5 | 19° |
| PP (Blue) | 0.8 | 0.5 | <0.1 | 18° |
| PP (Clear) | — | 0.3 | — | 18° |
| PVDF | 5.9 | 5.1 | 0.3 | 18° |
| PMMA | 3.5 | 2.0 | 0.2 | 18° |

It can be seen from Tables 20 and 21 that the monomer pre-soak process improvement greatly enhances % $W_g$, the amount and efficiency of PVP grafting as compared with no monomer pre-soak.

PVP Graft on PDMSO

Figure 4:
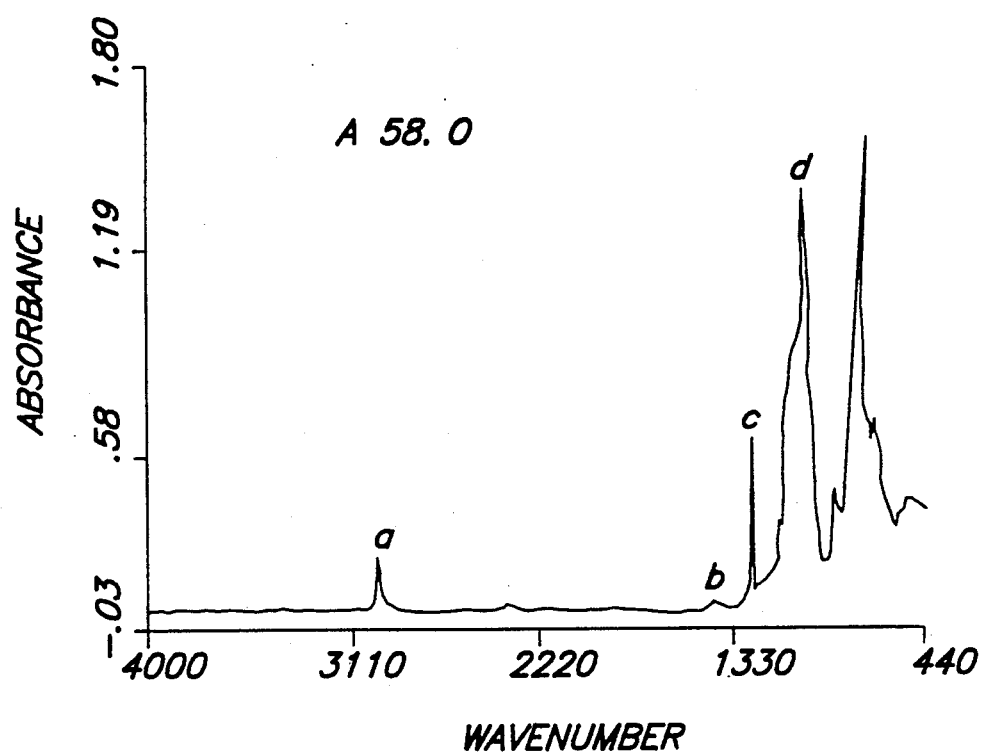
FIGS. 4–13 depict spectral analyses of various of the products according to the present invention.

FIG. 4 illustrates the FTIR/ATR spectrum of ungrafted silicone (PDMSO). FTIR/ATR gives surface composition information to depths of a micron or more.

Figure 5:
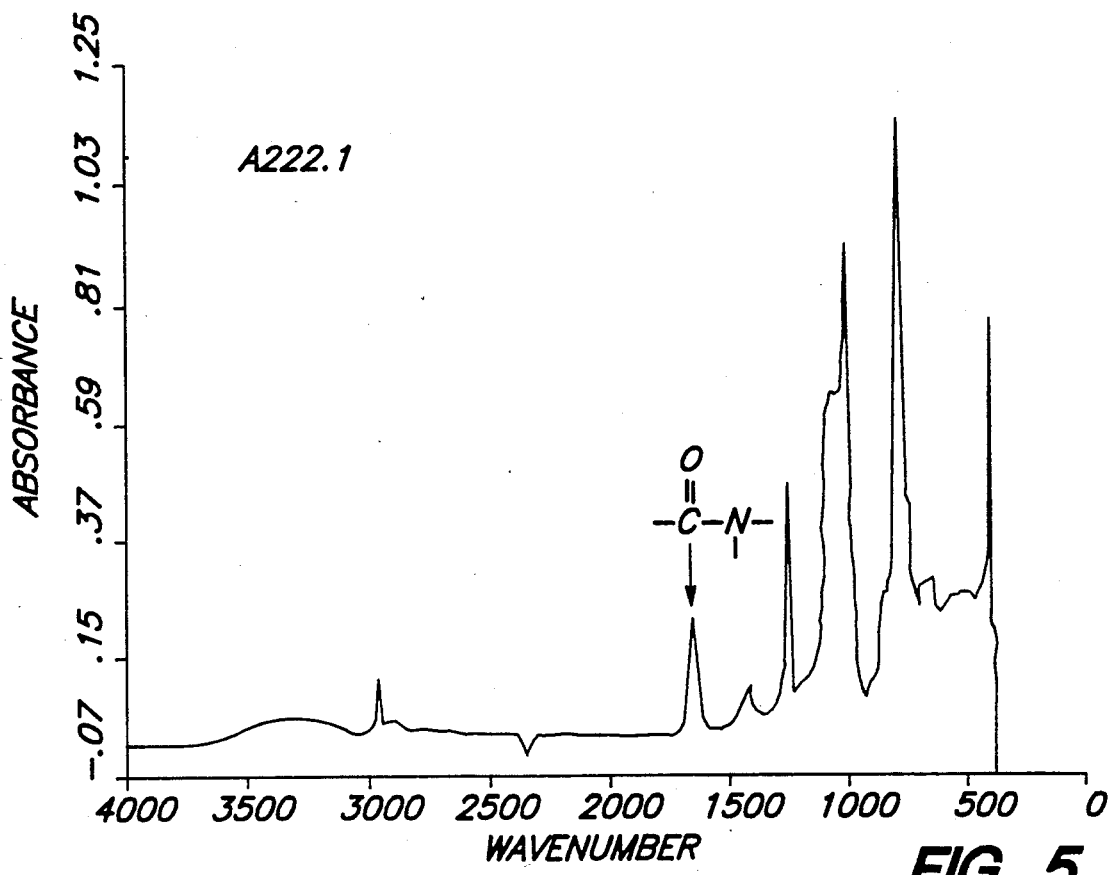
Figure 6:
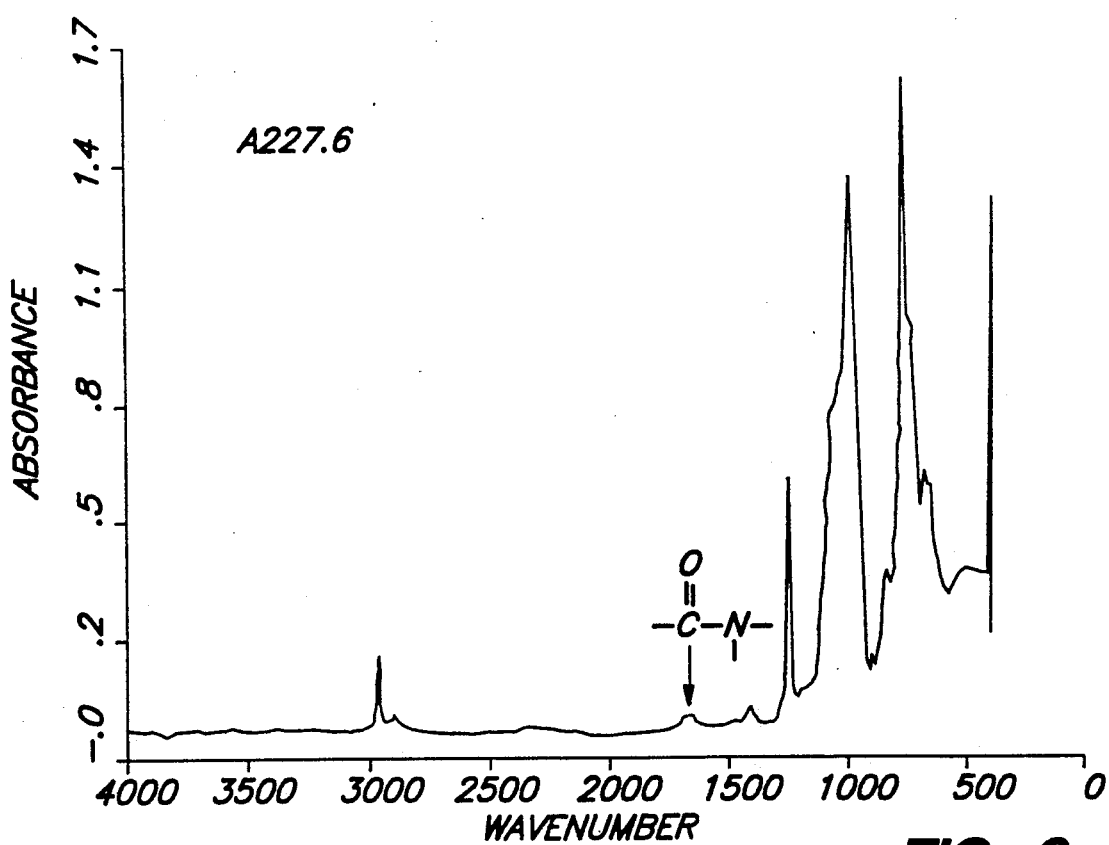

FIGS. 5 and 6 show the spectra for PVP-grafted PDMSO prepared by Methods A and B, respectively. The main feature in these spectra is the appearance of the absorption band at 1658 cm$^{-1}$ which corresponds to the carbonyl of the amide group of PVP. The relative intensities of the carbonyl peaks show that Method A is more efficient for grafting than Method B. This result is in good agreement with the gravimetric analysis and the dye uptake. However, both methods are more efficient than grafting without the monomer pre-soak.

PVP-g-PVDF

Figure 7:
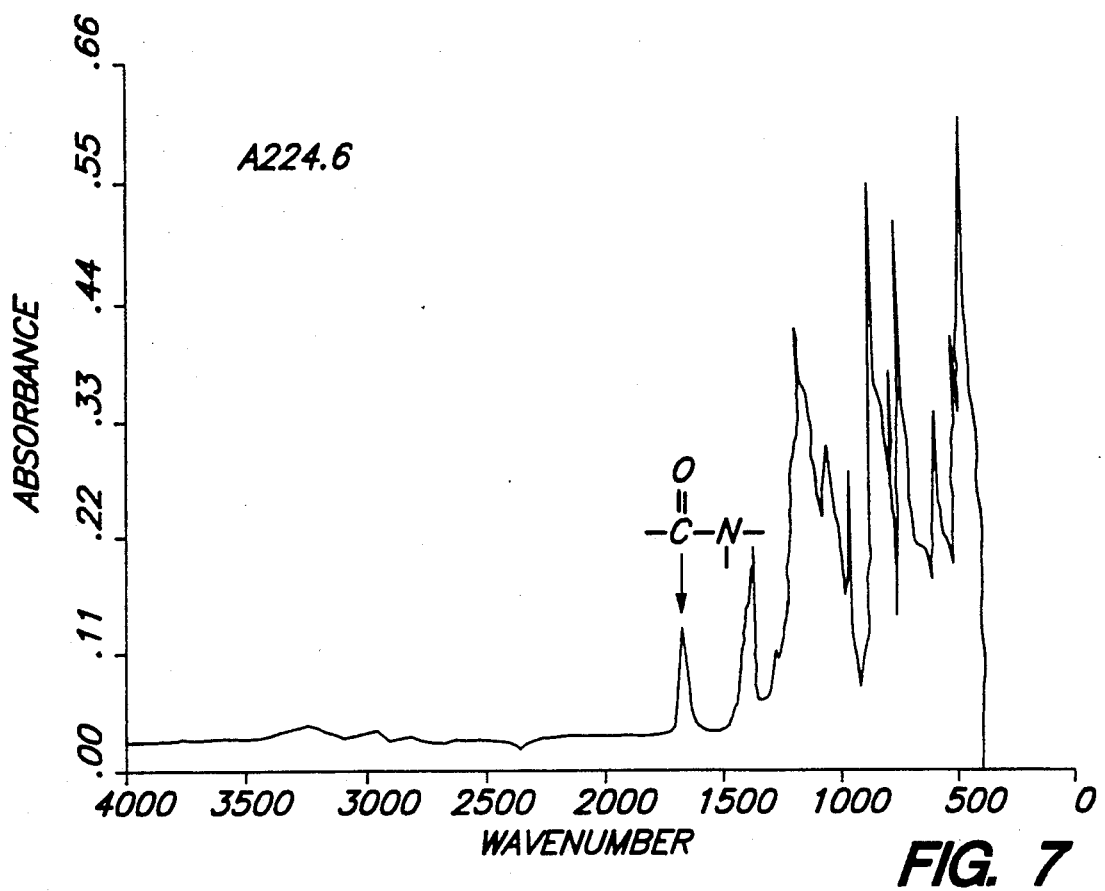
Figure 8:
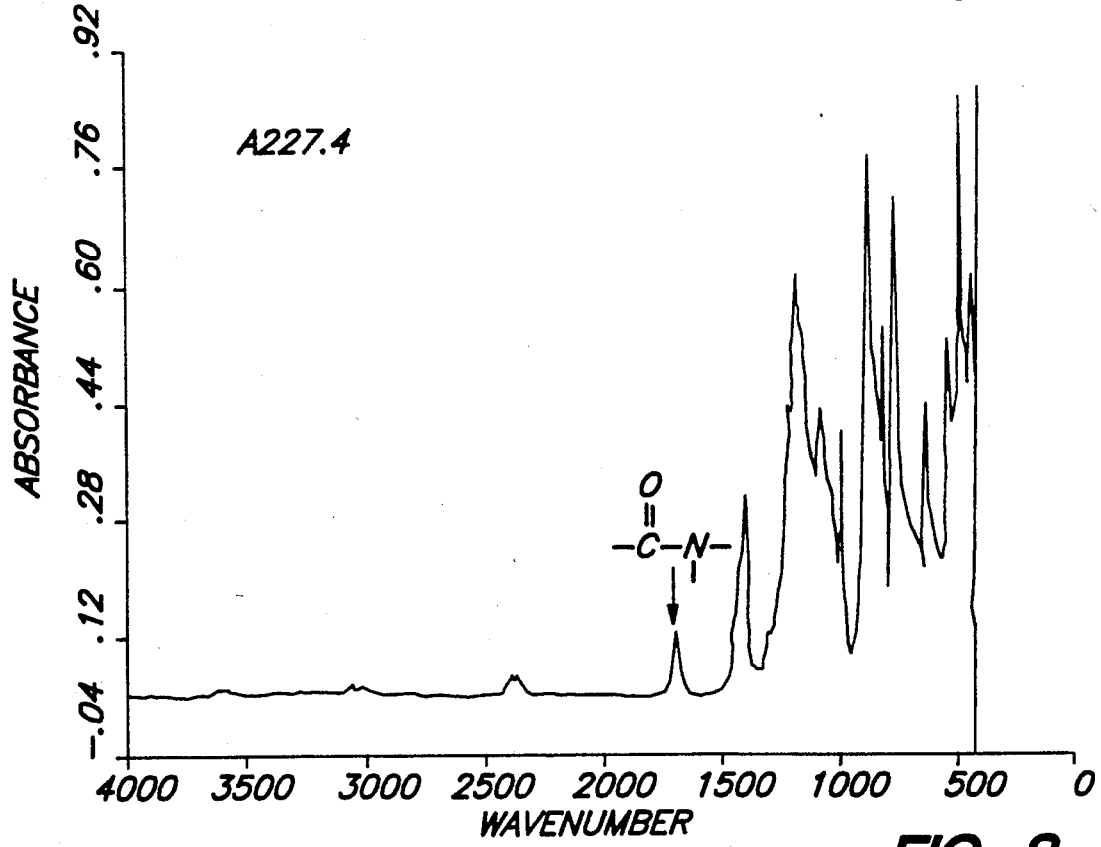

FIGS. 7 and 8 show the FTIR/ATR spectra for the PVP-g-PVDF graft system according to Methods A and B, respectively. Relative intensities of the carbonyl peaks are in good agreement with the gravimetric analysis and follow the same pattern as PVP-g-PDMSO.

Using Method C for PDMSO in which a 100% monomer pre-soak for 24 hours at 25° C. is used prior to gamma grafting using 10% aqueous NVP at 0.15 Mrad, even more efficient highly hydrophilic grafts may be achieved as indicated in Table 22. Additionally, as illustrated for PDMSO, graft efficiency can be further enhanced using a pre-soak with one monomer (100% cationic DMAEMA, for example) followed by gamma graft polymerization in a second monomer (10% aqueous NVP).

TABLE 22

Grafting of PVP on PDMSO by Method C
Pre-soak in 100% NVP or in 100%
second monomer system at 25° for 24 hrs.,
Grafting in 10% NVP with 0.15 Mrad.

| Pre-soak Monomer | % Graft ($W_g$) | Air Bubble Contact Angle |
|---|---|---|
| 100% NVP | 7.0 | 20° |
| 100% DMAEMA | 20.4 | 20° |
| 100% DMAEMA/NVP (50/50) | 9.7 | 20° |
| No pre-soak | 5.0 | 20°* |

*May be less stable and increase somewhat with time on prolonged aqueous immersion as compared with pre-soak grafts on PDMSO.

It can be seen from Table 22 that DMAEMA pre-soak of Method C prior to PVP grafting is an even more efficient gamma graft system. The pre-soak improvement also provides a more stable hydrophilic surface with virtually no change with time as compared to the non-pre-soak grafted PDMSO.

PVP-g-PP

Figure 9:
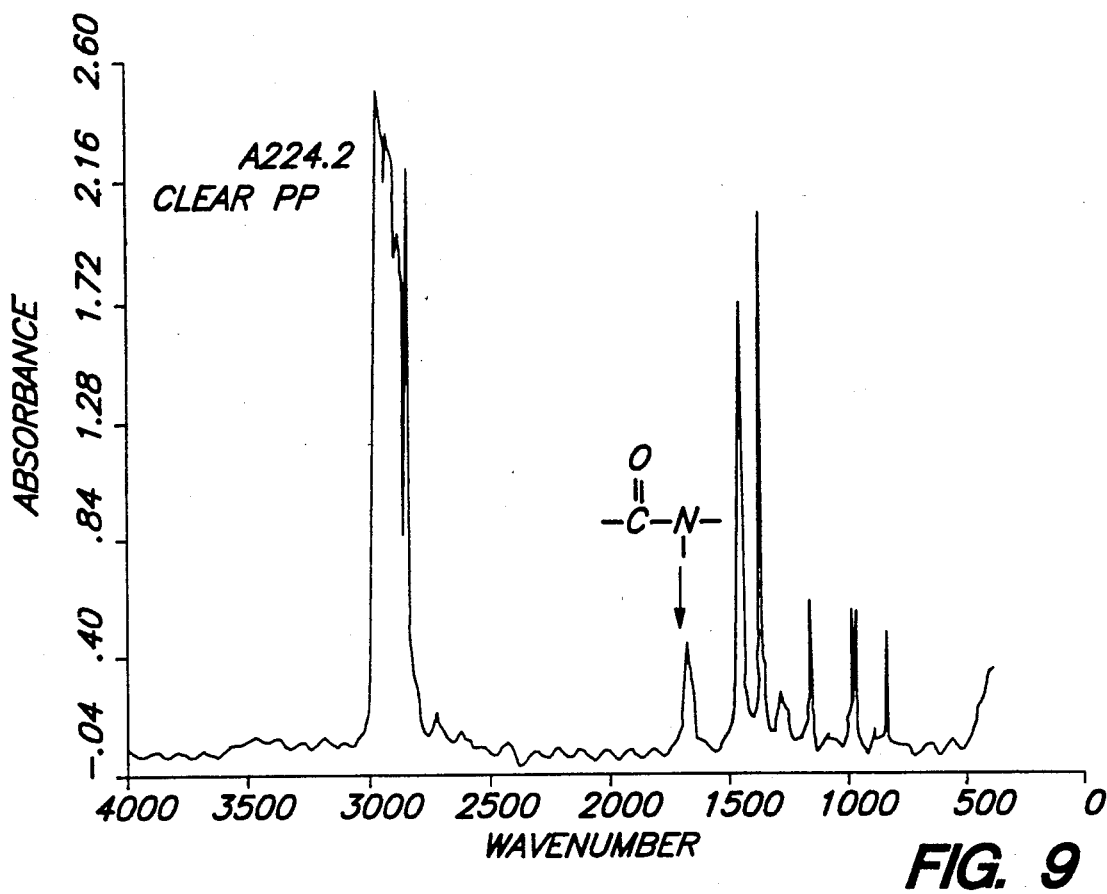
Figure 10:
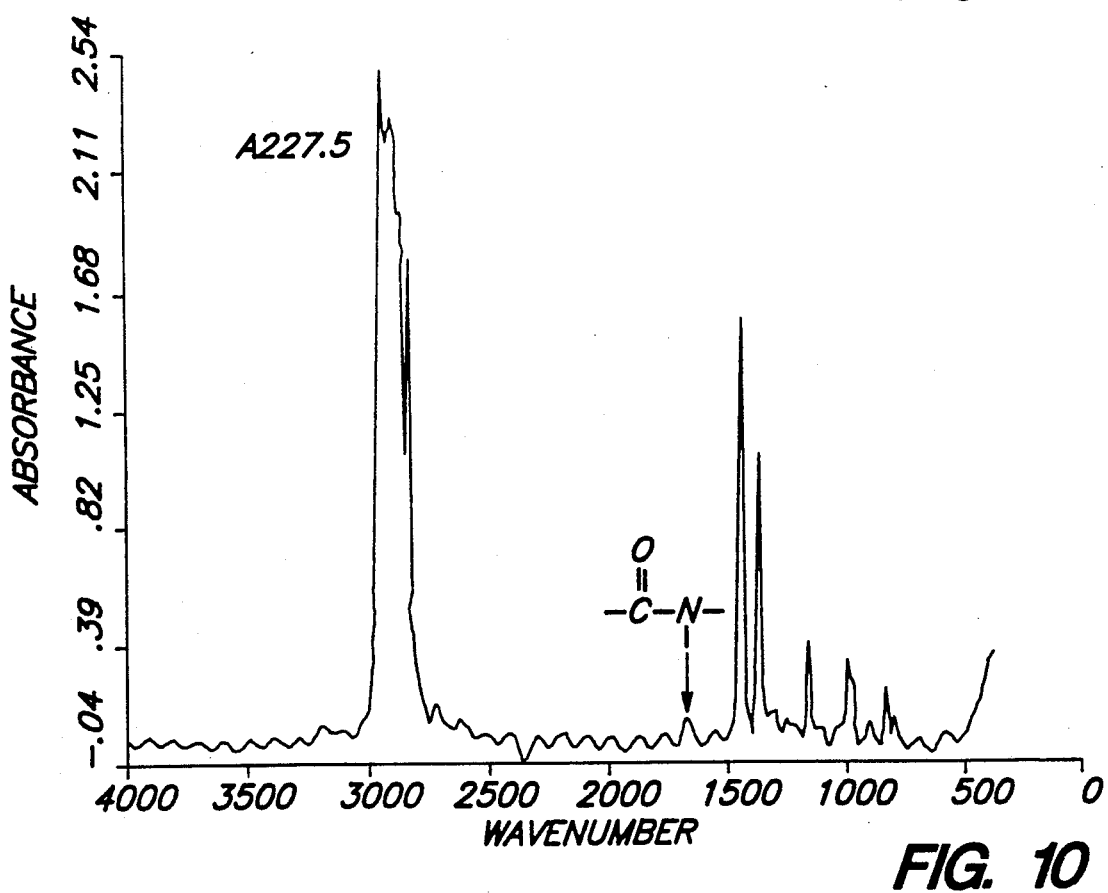
Figure 11:
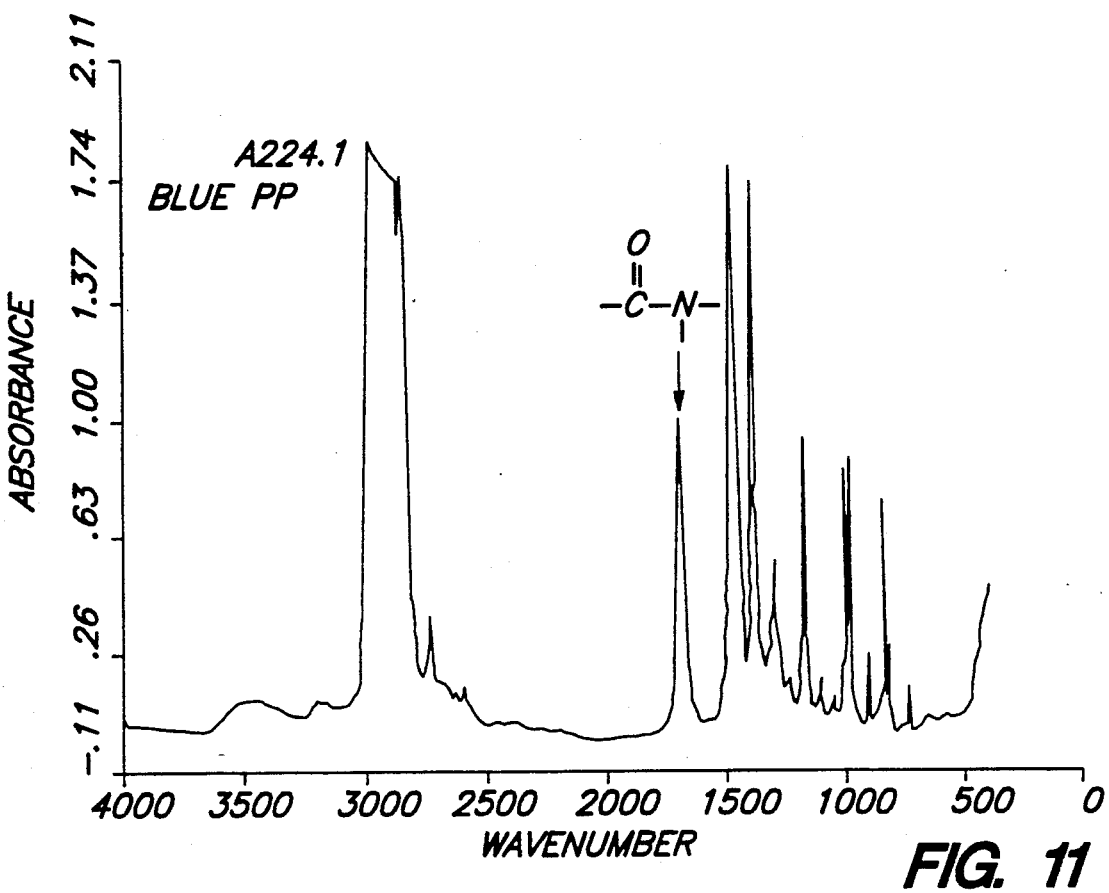
Figure 12:
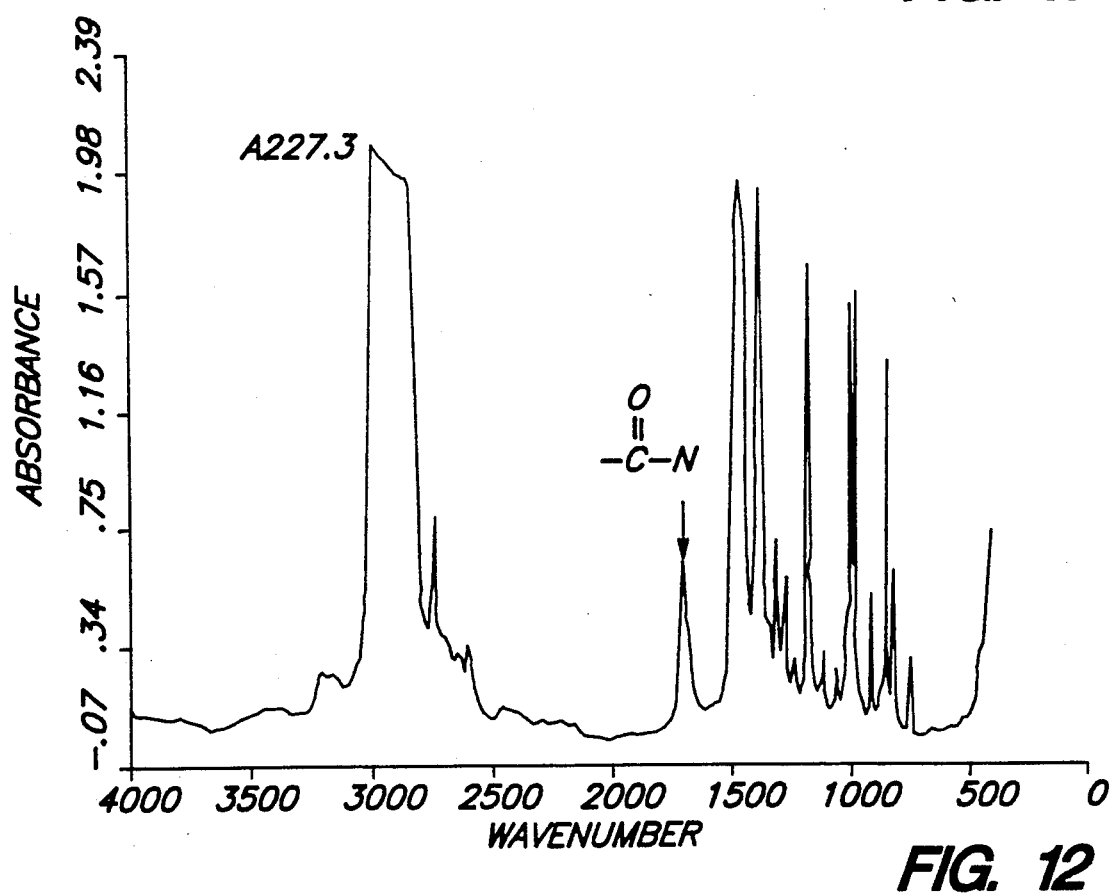

FTIR/ATR spectra for both clear (FIGS. 8 and 9) and blue PP (FIGS. 11 and 12) show substantial grafting by both Methods A and B.

PVP-g-PMMA

Figure 13:
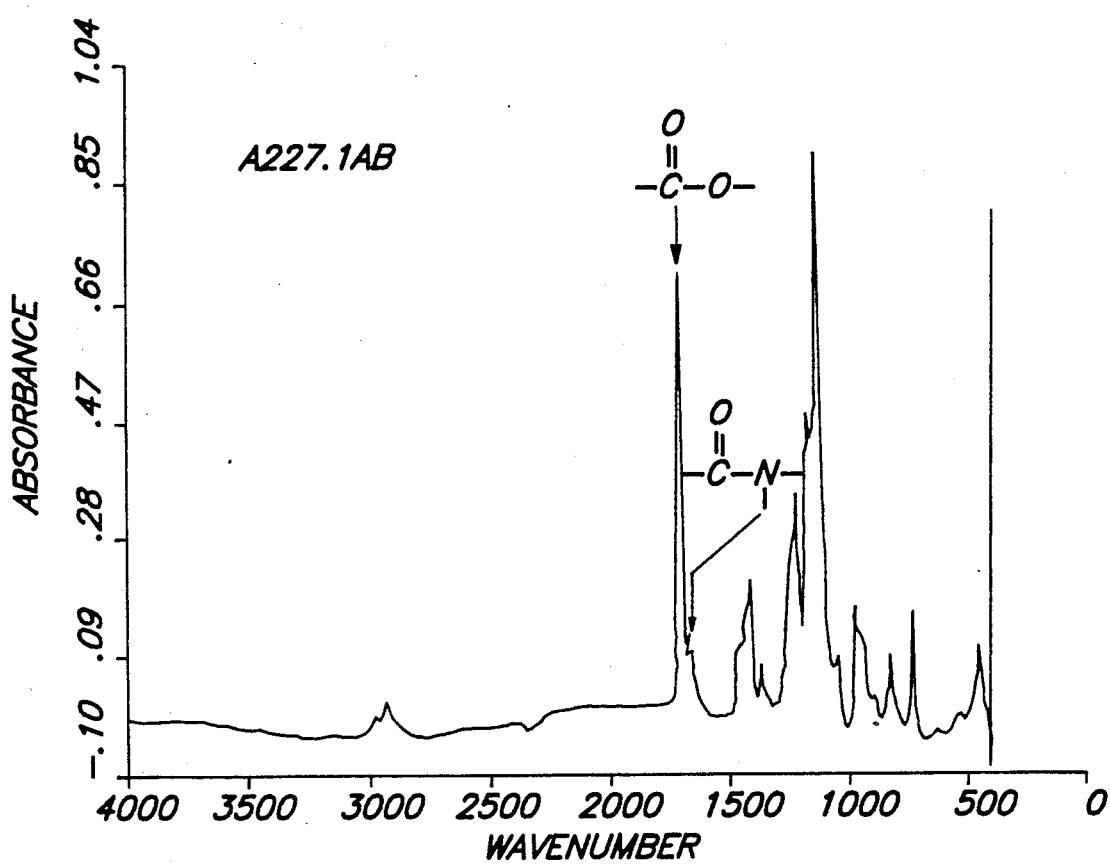

FIG. 13 shows the FTIR/ATR spectrum of PVP-g-PMMA using Method B. The PVP carbonyl (1658 $cm^{-1}$) is clearly distinguishable from the ester carbonyl (1725 $cm^{-1}$) of the substrate. Optical microscopy of this graft shows the uniform and optically clear graft surface modification up to about 150 m thick achieved by the pre-soak method of this invention.

Gravimetric measurements (Table 21), light microscopy and FTIR/ATR indicate the significant grafting achieved and support the concept of an IPN type of graft resulting from pre-soak diffusion penetration of monomer into the substrate.

Method B is of particular interest for the hydrophilic surface modification of PMMA since no swelling agents or radical inhibitors are needed.

PVP/SSA-g-PMMA

Table 23 summarizes data showing the improvement achieved by the pre-soak method for an anionic copolymer graft using a mixture of NVP and the anionic comonomer, styrene sulfonic acid (SSA). In this example, a total aqueous monomer solution concentration of 20% NVP with 10% SSA-Na salt was used. PMMA was pre-soaked with this comonomer solution at room temperature (ca. 25° C.) for various periods of time prior to gamma radiation grafting at a dose rate of about 700 rads/min in the same comonomer solution.

TABLE 23

Effect of Pre-soak for PVP/SSA-g-PMMA
Varying Radiation Dose and Pre-soak Time

| Pre-soak (hrs.) | Grafting Dose (Mrad) | Air Bubble Contact Angle | % Graft (Gravimetric) |
|---|---|---|---|
| 0 | 0.1 | 50° | <0.1 |
| 0 | 0.2 | 48° | <0.1 |
| 6 | 0.2 | 21° | 0.2 |
| 12 | 0.2 | <10° | 0.1 |
| 12 | 0.15 | 11° | 0.2 |
| 24 | 0.15 | <10° | 0.3 |

As shown in Table 23, the pre-soaking with the 30% NVP/SSA (2:1) comonomer solution affects a large increase in graft efficiency as indicated by the significantly increased hydrophilicity and the greater % grafting. Additionally, the solution polymer molecular weight and the solution viscosity even at 0.2 Mrad is low facilitating effective washing of the graft surface.

PVP/SSA-g-PDMSO

Table 24 summarizes data showing the improvement achieved by the pre-soak method using 100% NVP pre-soak for an anionic copolymer graft on silicone using a mixture of NVP and styrene sulfonic acid (SSA). PDMSO was pre-soaked in 100% NVP at about 25° C. for 24 hours prior to immersing the PDMSO in the aqueous comonomer solution and gamma irradiating at a dose rate of about 700 rads/min. SSA was used as the sodium salt (NaSSA).

TABLE 24

Effect of Pre-Soak for PVP/NaSSA-g-PDMSO Using 100% NVP Pre-soak
(24 hrs. at 25°) Followed by Aqueous PVP/NaSSA Grafting

| Grafting Dose (Mrad) | NVP Pre-Soak | % NaSSA | % NVP | % $W_g$ | Air Bubble Contact Angle |
|---|---|---|---|---|---|
| 0.05 | No | 20 | 20 | <0.1% | 17° |
| 0.05 | Yes | 20 | 20 | 4% | 13° |

Anionic PVP/NaSSA grafting was significantly enhanced by using a prior pre-soak of the polysiloxane in NVP, especially at the very low graft dose of 0.05 Mrad as indicated by the much greater PVP/NaSSA polymer graft weight and the lower contact angle achieved for the anionic copolymer graft. Using this improved pre-soak method, the 40% wt. aqueous comonomer system, containing 50% NaSSA with 50% NVP, also yields relative low solution viscosities which favors easy washing of grafts.

EXAMPLE 15

Intraocular lenses (IOLs) are readily surface modified using conditions described in the above examples and implanted in rabbit eyes for periods of up to one year to demonstrate the good bio-acceptance of the hydrophilic gamma polymerization surface modified IOL ocular implants prepared by the process conditions of this invention. For example, Sinskey-style-037 J-loop lenses (PMMA optics/PP haptics), surface modified with PVP, ethylene oxide sterilized and implanted in the anterior chambers, and one-piece flexible haptic PMMA IOLs implanted in the posterior chambers of New Zealand white rabbits show good biocompatibility. Process conditions for the pre-soak process improvement for IOL surface modifications are preferably according to Method B of Example 14.

Periodic slit lamp examinations of eyes, histopathology after one year and microscopic examination of explanted lenses (compared to ungrafted PMMA control IOLs), indicate good biocompatibility for the hydrophilic polymer surface graft modifications of this invention.

We claim:

1. A method for modifying the surface of an ocular implant material, said surface comprising polymethylmethacrylate (PMMA), polypropylene (PP), polyvinylidene fluoride (PVDF), a polycarbonate (PC), a polysulfone (PSF) or a silicone polymer (PDMSO), by the gamma-irradiation induced graft polymerization coating thereon of:
   1) a monomer comprising N-vinylpyrrolidone (NVP),
   2) a monomer comprising 2-hydroxyethyl-methacrylate (HEMA),
   3) a mixture comprising (NVP) and (HEMA), (NVP-HEMA), or
   4) a mixture of 1), 2) or 3) with up to about 50 wt %, based on the total monomer weight, of an ionic monomer, salt of an ionic monomer or mixture thereof; so as to form a hydrophilic graft polymer coating of:
   I. polyvinylpyrrolidone (PVP),
   II. poly-2-hydroxyethylmethacrylate (PHEMA),
   III. a copolymer of (NVP) and (HEMA), [P(NVP-HEMA)], or
   IV. a copolymer of (NVP), (HEMA) or (NVP-HEMA) and said ionic monomer, on said surface, the improvement comprising:
   a) pre-soaking said ocular implant material in at least one of said monomers or in a first aqueous solution of at least one of said monomers, having a concentration of monomer therein of from about 5 to about 95%, by weight, and conducting said gamma-irradiation induced graft polymerization in a second aqueous solution of at least one of said monomers under the following conditions:
   b) monomer concentration in the range of from about 0.1% to about 50%, by weight;
   c) total gamma dose in the range of from about 0.001 to less than about 0.5 Mrad; and
   d) gamma dose rate in the range of from about 10 to about 2500 rads/min;
   said pre-soaking in step a) being conducted for a period of time and at a temperature sufficient to facilitate diffusion of said monomer or monomers into said ocular implant material.

2. The method of claim 1 further including one or more of the following conditions:
   (e) substantially excluding free oxygen from said graft polymerization solution;
   (f) maintaining the thickness of said polymer coating in the range of from about 100 Å to about 100 microns;
   (g) including a free radical scavenger in said aqueous graft polymerization solution; and
   (h) including in said aqueous graft polymerization solution a swelling solvent for said PMMA surface.

3. The method of claim 1 wherein said pre-soaking step is conducted at a temperature in the range of from about 25° to about 90° C.

4. The method of claim 1 wherein said pre-soaking is conducted for a period of time from about 0.25 to about 48 hours.

5. The method of claim 1 wherein said ocular implant material is an intraocular lens.

6. The method of claim 1 wherein said ocular implant material is a corneal inlay.

7. The method of claim 1 wherein said ocular material is a keratoprosthesis.

8. The method of claim 1 wherein said ocular material is a glaucoma shunt.

9. The method of claim 1 wherein said ionic monomer is a vinylsulfonic acid, a vinylcarboxylic acid or a salt thereof.

10. The method of claim 9 wherein said vinylcarboxylic acid is acrylic, methacrylic or crotonic acid.

11. The method of claim 9 wherein said vinylsulfonic acid is sulfoethylmethacrylate, sulfopropylmethacrylate, styrene sulfonic acid or vinylsulfonic acid.

12. The method of claim 1 wherein said ionic monomer is an amino-functional monomer.

13. The method of claim 12 wherein said amino-functional monomer is a vinylpyridine, an amino-styrene, an aminoacrylate or an aminomethacrylate.

14. An ocular implant prepared according to the method of claim 1.

15. An ocular implant according to claim 13 wherein said ocular implant is an intraocular lens, a corneal inlay, a keratoprosthesis, an epikeratophakia device, a glaucoma shunt, a retinal staple or a scleral buckle.

16. A method for modifying the surface of an ocular implant material, said surface comprising polymethylmethacrylate (PMMA), polypropylene (PP), polyvinylidene fluoride (PVDF), a polycarbonate (PC), a polysulfone (PSF) or a silicone polymer (PDMSO), by the electron beam irradiation induced graft polymerization coating thereon of:
   (1) a monomer comprising N-vinylpyrrolidone (NVP),
   (2) a monomer comprising 2-hydroxyethylmethacrylate (HEMA),
   (3) a mixture comprising (NVP) and (HEMA), (NVP-HEMA), or
   (4) a mixture of (1), (2) or (3) with up to about 50 wt %, based on the total monomer weight, of an ionic monomer, salt of an ionic monomer or mixture thereof; so as to form a hydrophilic graft polymer coating of:
   I. polyvinylpyrrolidone (PVP),
   II. poly-2-hydroxyethylmethacrylate (PHEMA),
   III. a copolymer of (NVP) and (HEMA), [P(NVP-HEMA)], or
   IV. a copolymer of (NVP), (HEMA) or (NVP-HEMA) and said ionic monomer, on said surface, comprising:
   (a) pre-soaking said ocular implant material in at least one of said monomers or in a first aqueous solution of at least one of said monomers, having a concentration of monomer therein of from about 5 to about 95%, by weight, and conducting said electron-beam irradiation induced graft polymerization in a second aqueous solution of at least one of said monomers under the following conditions:
   (b) monomer concentration in the range of from about 0.1% to about 50%, by weight;
   (c) total electron beam irradiation dose in the range of from about 0.001 to less than about 0.50 Mrad; and
   (d) electron beam irradiation dose rate in the range of from about 10 to about $10^8$ rads/min;

said pre-soaking in step (a) being conducted for a period of time and at a temperature sufficient to facilitate diffusion of said monomer or monomers into said ocular implant material.

17. The method of claim 16 further including one or more of the following conditions:

(e) substantially excluding free oxygen from said graft polymerization solution;

(f) maintaining the thickness of said polymer coating in the range of from about 100 Å to about 100 microns;

(g) including a free radical scavenger in said aqueous graft polymerization solution; and (h) including in said aqueous graft polymerization solution a swelling solvent for said PMMA surface.

* * * * *